US012614610B2

(12) United States Patent
Balijepalli et al.

(10) Patent No.: US 12,614,610 B2
(45) Date of Patent: Apr. 28, 2026

(54) AGILE NUCLEIC ACID SENSOR AND MEASURING A BIOMARKER

(71) Applicant: Government of the United States of America, as represented by the Secretary of Commerce, Gaithersburg, MD (US)

(72) Inventors: Arvind Kumar Balijepalli, Washington, DC (US); Jacob Michael Majikes, Gaithersburg, MD (US); Alokik Kanwal, Gaithersburg, MD (US); Peter Michael Vallone, Potomac, MD (US); Kevin Michael Kiesler, Rockville, MD (US); Erica Lee Romsos, Ijamsville, MD (US); Anthony José Kearsley, Hanover, MD (US)

(73) Assignee: GOVERNMENT OF THE UNITED STATES OF AMERICA, AS REPRESENTED BY THE SECRETARY OF COMMERCE, Gaithersburg, MD (US)

( * ) Notice: Subject to any disclaimer, the term of this patent is extended or adjusted under 35 U.S.C. 154(b) by 923 days.

(21) Appl. No.: 17/845,682

(22) Filed: Jun. 21, 2022

(65) Prior Publication Data
US 2022/0325332 A1     Oct. 13, 2022

Related U.S. Application Data

(63) Continuation-in-part of application No. 17/360,008, filed on Jun. 28, 2021, now Pat. No. 12,195,787.
(Continued)

(51) Int. Cl.
*G16B 25/30*     (2019.01)
*B01L 3/00*     (2006.01)
(Continued)

(52) U.S. Cl.
CPC ........ *G16B 25/30* (2019.02); *B01L 3/502715* (2013.01); *G16B 25/00* (2019.02); *C12Q 1/6825* (2013.01)

(58) Field of Classification Search
CPC ... G16B 25/30; G16B 25/00; B01L 3/502715; C12Q 1/6825; B82Y 15/00
See application file for complete search history.

(56) References Cited

U.S. PATENT DOCUMENTS

| | | | |
|---|---|---|---|
| 10,718,732 B2 * | 7/2020 | Levine | H01L 23/53261 |
| 2018/0258469 A1 * | 9/2018 | Johnson-Buck | |
| | | | G01N 33/54306 |

(Continued)

OTHER PUBLICATIONS

Grieshaber et al. (Electrochemical Biosensors—Sensor Principles and Architectures, Sensors 2008, 8, 1400-1458) (Year: 2008).*
(Continued)

*Primary Examiner* — Larry D Riggs, II
*Assistant Examiner* — Ghazal Sabour
(74) *Attorney, Agent, or Firm* — Office of Chief Counsel for National Institute of Standards and Technology

(57) ABSTRACT

An agile nucleic acid sensor includes: a DNA switch; an analysis substrate in electrostatic communication with the DNA switch and that produces a biomarker electrical signal; a transduction member that receives the biomarker electrical signal and produces a transduction signal; a sensor counter electrode in electrical communication with and capacitively coupled to the analysis substrate and that receives a counter electrode voltage; a sensor reference electrode in electrical communication and capacitively coupled to the analysis substrate and that produces a feedback signal based on electrical interactions with a composition that is in fluid contact with the feedback signal and the analysis substrate; and a voltage follower in electrical communication with the sensor counter electrode and the sensor reference electrode
(Continued)

and that receives the feedback signal from the sensor reference electrode and produces the counter electrode voltage for the sensor counter electrode based on the feedback signal.

2 Claims, 19 Drawing Sheets

Related U.S. Application Data

(60) Provisional application No. 63/212,753, filed on Jun. 21, 2021, provisional application No. 63/045,366, filed on Jun. 29, 2020.

(51) Int. Cl.
 *C12Q 1/6825* (2018.01)
 *G16B 25/00* (2019.01)

(56) References Cited

U.S. PATENT DOCUMENTS

| | | |
|---|---|---|
| 2019/0137443 A1 | 5/2019 | Balijepalli et al. |
| 2020/0264129 A1 | 8/2020 | Balijepalli et al. |
| 2021/0088463 A1 | 3/2021 | Balijepalli et al. |

OTHER PUBLICATIONS

Zhang et al. (Control of DNA Strand Displacement Kinetics Using Toehold Exchange, Article, Nov. 6, 2009, pp. 17303-17314) (Year: 2009).*

GIS AID, SARS-CoV2 Variants, Accessed Jun. 17, 2022, DOI: https://www.gisaid.org/hcov19-variants/.

Majikes, J.M., et al., "Revealing thermodynamics of DNA origami folding via affine transformations", Nucleic Acids Research, 2020, p. 5268-5280, vol. 48 No. 10.

Zhang, D.Y., et al., "Dynamic DNA nanotechnology using strand-displacement reactions", Nature Chemistry, 2011, p. 103-113, vol. 3.

Brown, S., et al., "An easy-to-prepare mini-scaffold for DNA origami", Nanoscale, 2015, p. 16621-16624, vol. 7.

Guros, N.B., et al., "Reproducible Performance Improvements to Monolayer MoS2 Transistors through Exposed Material Forming Gas Annealing", ACS Applied Materials and Interfaces, 2019, p. 16683-16692, vol. 11.

Le, S.T., et al., "Rapid, quantitative therapeutic screening for Alzheimer's enzymes enabled by optimal signal transduction with transistors", Analyst, 2020, p. 2925-2936, vol. 145.

Le, S.T., et al., "Quantum capacitance-limited MoS2 biosensors enable remote label-free enzyme measurements", Nanoscale, 2019, p. 15622-15632, vol. 11.

Kanwal, A., et al., "Scalable nano-bioprobes with sub-cellular resolution for cell detection", Biosensors and Bioelectronics, 2013, p. 267-273, vol. 45.

Evans, R.M., et al., "Diffusion-Limited Reactions in Nanoscale Electronics", Methods and Applications of Analysis, 2019, p. 149-166, vol. 26 No. 2.

Moorthy, A.S., et al., "Mass spectral similarity mapping applied to fentanyl analogs", Forensic Chemistry, 2020, p. 100237, vol. 19.

Kearsley, A.J., et al., "Stochastic regression modeling of chemical spectra", Chemometrics and Intelligent Laboratory Systems, 2014, p. 26-32, vol. 139.

Patrone, P.N., et al., "Affine analysis for quantitative PCR measurements", Analytical and Bioanalytical Chemistry, 2020, p. 7977-7988, vol. 412.

Infectious Disease In Vitro Diagnostics Market Size, Share & Trends Analysis Report By Product (Instruments, Reagents), by Application (HPV, HIV), by Technology, by Test Location, and Segment Forecasts, 2022-2030, Report ID: 978-1-68038-716-2, Historical Range: 2018-2020, Accessed Aug. 30, 2022 DOI: https://www.grandviewresearch.com/industry-analysis/ivd-infectious disease-market.

Biden, J., "A Letter to Dr. Eric S. Lander, the President's Science Advisor and nominee as Director of the Office of Science and Technology Policy", Statements and Releases, 2021, Accessed Jun. 17, 2022, DOI: https://www.whitehouse.gov/briefingroom/statements-releases/2021/01/20/a-letter-to-dr-eric-s-lander-the-presidents-science-advisorand-nominee-as-director-of-the-office-of-science-and-technology-policy/.

Seo, J.H., et al., "The market trend analysis and prospects of cancer molecular diagnostics kits", Biomaterials Research, 2018, vol. 22.

Yan, J., et al., "Novel Rolling Circle Amplification and DNA Origami-Based DNA Belt-Involved Signal Amplification Assay for Highly Sensitive Detection of Prostate-Specific Antigen (PSA)", ACS Applied Materials & Interfaces, 2014, p. 20372-20377, vol. 6.

Zhao, W.-W. et al., "Exciton-Plasmon Interactions between CdS Quantum Dots and AgNanoparticles in Photoelectrochemical System and Its Biosensing Application", Analytical Chemistry, 2012, p. 5892-5897, vol. 84.

Golub, E., et al., "Electrochemical, Photoelectrochemical, and Surface Plasmon Resonance Detection of Cocaine UsingSupramolecular Aptamer Complexes and Metallic or Semiconductor Nanoparticles", Anal.Chem., 2009, p. 9291-9298, vol. 81.

Sakata, T., et al., "Detection sensitivity of genetic field effect transistor combinedwith charged nanoparticle-DNA conjugate", International Conference on Microtechnologies in Medicine and Biology, 2006, p. 97-100, doi: 10.1109/MMB.2006.251500.

Wang, X. et al., "Tetrahedral DNA Nanostructure-decorated Electrochemical Platform forSimple and Ultrasensitive EGFR Genotyping of Plasma ctDNA", Analyst, 2020, p. 4671-4679, vol. 145, doi:10.1039/D0AN00591F.

Liu, Y., et al., "Tuning Biosensor Cross-Reactivity Using Aptamer Mixtures", Analytical Chemistry, 2020, p. 5041-5047, vol. 92, doi: 10.1021/acs.analchem.9b05339.

Wu, D. et al., "Dual-Aptamer Modified Graphene Field-Effect Transistor Nanosensor forLabel-Free and Specific Detection of Hepatocellular Carcinoma-Derived Microvesicles", Anal. Chem., 2020, p. 4006-4015, vol. 92, doi: 10.1021/acs.analchem.9b05531.

Zhang, D. Y., et al., "Control of DNA Strand Displacement Kinetics Using Toehold Exchange", J. Am. Chem. Soc., 2009, p. 17303-17314, vol. 131.

Zhang, Z. et al., "A DNA-Origami chip platform for label-free SNP genotyping using toehold-mediated strand displacement", Small, 2010, p. 1854-1858, vol. 6 No. 17.

Hiwang, M. T. et al., "Highly specific SNP detection using 2D graphene electronics andDNA strand displacement", PNAS, 2016, p. 7088-7093, vol. 113 No.26.

Chan, M. S. et al., "Reversible reconfiguration of high-order DNA nanostructures byemploying G-quartet toeholds as adhesive units", Nanoscale, 2020, p. 2464-2471, vol. 12.

Hu, P. et al., "Cooperative Toehold: A Mechanism to Activate DNA Strand Displacementand Construct Biosensors", Analytical Chemistry, 2018, p. 9751-9760, vol. 90.

Chandrasekaran, A. R. et al., "DNA nanotechnology approaches for microRNA detection and diagnosis", Nucleic Acids Research, 2019, p. 10489-10505, vol. 47 No. 20.

Puchkova, A. et al., "DNA Origami Nanoantennas with over 5000-fold FluorescenceEnhancement and Single-Molecule Detection at 25 μM", Nano Letters, 2015, p. 8354-8359, vol. 15.

Daems, D. et al., "Three-Dimensional DNA Origami as Programmable Anchoring Points for Bioreceptors in Fiber Optic Surface Plasmon Resonance Biosensing", ACS Applied Materials and Interfaces, 2018, p. 23539-23547, vol. 10.

* cited by examiner (A)

(B)

(A) <u>210</u>

(B) <u>210</u>

(C)

(D) <u>210</u>

(E) <u>210</u>

(A)

(B)

Affine Transform

1

AGILE NUCLEIC ACID SENSOR AND MEASURING A BIOMARKER

CROSS REFERENCE TO RELATED APPLICATIONS

This application is a continuation-in-part and claims benefit of the following applications: U.S. Provisional Patent Application Ser. No. 63/212,753, filed Jun. 21, 2021; and U.S. patent application Ser. No. 17/360,008, filed Jun. 28, 2021, which claims benefit to Provisional Patent Application Ser. No. 63/045,366, filed Jun. 29, 2020, all of which are incorporated by reference in their entirety.

STATEMENT REGARDING FEDERALLY SPONSORED RESEARCH

This invention was made with United States Government support from the National Institute of Standards and Technology (NIST), an agency of the United States Department of Commerce. The Government has certain rights in this invention.

BRIEF DESCRIPTION

Disclosed is an agile nucleic acid sensor for measuring a biomarker, the agile nucleic acid sensor comprising: a DNA switch that contacts and selectively duplexes with a chemical analyte comprising the biomarker; an analysis substrate in electrostatic communication with the DNA switch that is disposed on the analysis substrate, such that when the chemical analyte duplexes with the DNA switch, the analysis substrate produces a biomarker electrical signal; a transduction member in electrical communication with the analysis substrate and that receives the biomarker electrical signal and produces a transduction signal in response to receiving the biomarker electrical signal; a sensor counter electrode in electrical communication with and capacitively coupled to the analysis substrate and that receives a counter electrode voltage; a sensor reference electrode in electrical communication and capacitively coupled to the analysis substrate and that produces a feedback signal based on electrical interactions with a composition that is in fluid contact with the feedback signal and the analysis substrate; and a voltage follower in electrical communication with the sensor counter electrode and the sensor reference electrode and that receives the feedback signal from the sensor reference electrode and produces the counter electrode voltage for the sensor counter electrode based on the feedback signal.

Disclosed is a process for measuring a biomarker with an agile nucleic acid sensor array, the process comprising: operating the agile nucleic acid sensor array that comprises: a plurality of agile nucleic acid sensors arranged in array and that individually comprise: a DNA switch; an analysis substrate in electrostatic communication with the DNA switch that is disposed on the analysis substrate; a transduction member in electrical communication with the analysis substrate; a sensor counter electrode in electrical communication with and capacitively coupled to the analysis substrate; a sensor reference electrode in electrical communication and capacitively coupled to the analysis substrate; and a voltage follower in electrical communication with the sensor counter electrode and the sensor reference electrode; for individual agile nucleic acid sensors in the agile nucleic acid sensor array: producing a counter electrode voltage by the voltage follower; subjecting the sensor counter electrode to the counter electrode voltage from the voltage follower;

2 contacting the DNA switch with a chemical analyte comprising the biomarker; producing, by the analysis substrate, a biomarker electrical signal in response to the chemical analyte contacting the DNA switch; receiving, by the transduction member, the biomarker electrical signal from the analysis substrate and producing a transduction signal from the biomarker electrical signal; determining the impedance of the sensor working electrode from the transduction signal; estimating kinetic rate constants for each contact between the chemical analyte and the DNA switch; and combining the kinetic rate constants and producing a mean kinetic rate constant with uncertainty quantification for the kinetic rate constants; aggregating the mean kinetic rate constants for the plurality of agile nucleic acid sensors in the agile nucleic acid sensor array; and producing a kinetic fingerprint for the chemical analyte from the mean kinetic rate constants.

BRIEF DESCRIPTION OF THE DRAWINGS

The following description cannot be considered limiting in any way. Various objectives, features, and advantages of the disclosed subject matter can be more fully appreciated with reference to the following detailed description of the disclosed subject matter when considered in connection with the following drawings, in which like reference numerals identify like elements.

DETAILED DESCRIPTION

Figure 1:
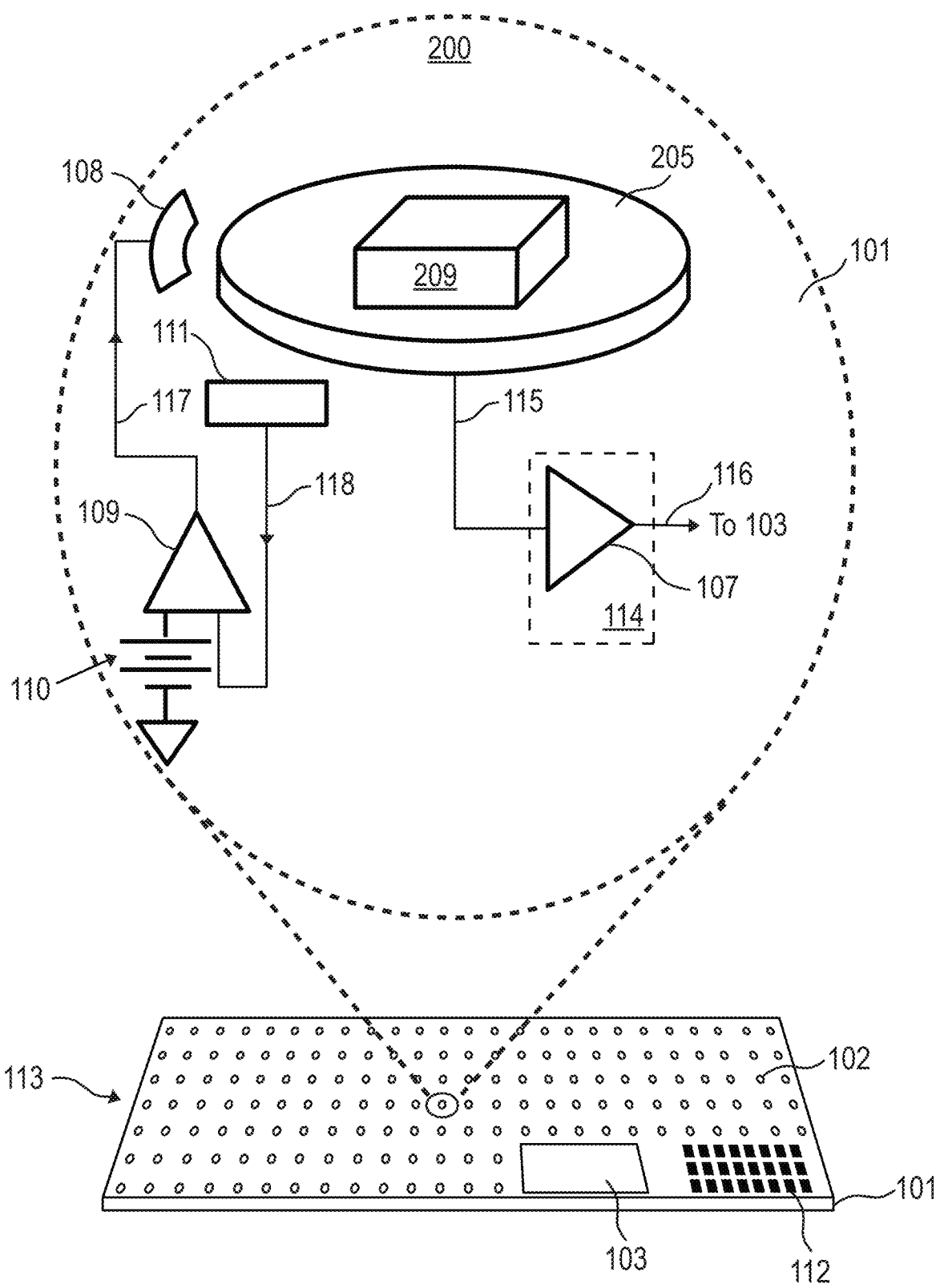
FIG. 1 shows an agile nucleic acid sensor, according to some embodiments.

A detailed description of one or more embodiments is presented herein by way of exemplification and not limitation.

Nucleic acids, e.g., DNA and RNA are building blocks for life. Mutations in nucleic acids from inherited or environmental factors can result in diseases such as cancers. Viruses employ rapid mutations to hijack cells and evade the immune system. Surveillance of nucleic acids can be used to monitor public health. Mutations in biomarkers can outpace development or deployment of high-specificity diagnostic tests. There is a need for a novel and agile biomarker metrology, as evidenced by pandemics such as attending spread of SARS CoV-2 mutants that challenged conventional diagnostic testing infrastructure. The agile nucleic acid sensor and process for measuring a biomarker disclosed herein meet this need and provide a biomarker metrology that combines DNA nanostructure-enhanced detectors with artificial intelligence (AI) frameworks with flexibility to allow rapid reprogramming in the field.

The agile nucleic acid sensor and process for measuring a biomarker have high sensitivity in an absence of polymerase chain reaction (PCR). PCR is a sample enrichment technique with disadvantages that include a significant wait for analysis results and system complexity. The agile nucleic acid sensor array disclosed herein involves DNA nanotechnology to make arrays of electronic sensors that produce unique molecular signatures for different chemical analytes. High-dimensional data including the unique molecular signatures are involved in decoding by AI methods and quantifying measurement errors and uncertainty (UQ). The agile nucleic acid sensor array is a reprogrammable label-free and PCR-free biomarker detection chip that can be used in many areas such as medical diagnostics and surveillance of public health threats.

Agile nucleic acid sensor 200 measures a biomarker. In an embodiment, with reference to FIG. 1, FIG. 2, FIG. 3, FIG. 4, FIG. 5, FIG. 6, FIG. 7, FIG. 8, FIG. 9, FIG. 10, and FIG. 11, agile nucleic acid sensor 200 includes: a DNA switch 209 that contacts and selectively duplexes with a chemical analyte 203 including the biomarker; an analysis substrate 205 in electrostatic communication with the DNA switch 209 that is disposed on the analysis substrate 205, such that when the chemical analyte 203 duplexes with the DNA switch 209, the analysis substrate 205 produces a biomarker electrical signal 115; a transduction member 114 in electrical communication with the analysis substrate 205 and that receives the biomarker electrical signal 115 and produces a transduction signal 116 in response to receiving the biomarker electrical signal 115; a sensor counter electrode 108 in electrical communication with and capacitively coupled to the analysis substrate 205 and that receives a counter electrode voltage 117; a sensor reference electrode 111 in electrical communication and capacitively coupled to the analysis substrate 205 and that produces a feedback signal 118 based on electrical interactions with a composition that is in fluid contact with the feedback signal 118 and the analysis substrate 205; and a voltage follower 109 in electrical communication with the sensor counter electrode 108 and the sensor reference electrode 111 and that receives the feedback signal 118 from the sensor reference electrode 111 and produces the counter electrode voltage 117 for the sensor counter electrode 108 based on the feedback signal 118.

Figure 3:
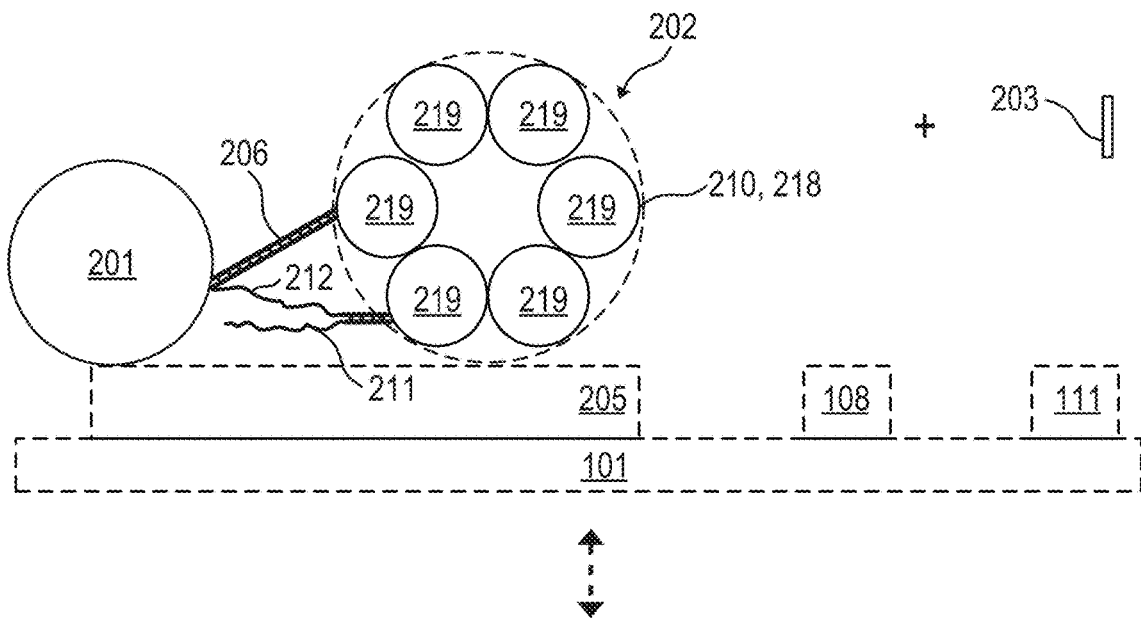
FIG. 3 shows a DNA switch before binding a chemical analyte in panel A and after binding the chemical analyte in panel B, wherein the DNA switch is configured for robust signal amplification upon analyte binding, according to some embodiments.
Figure 3:
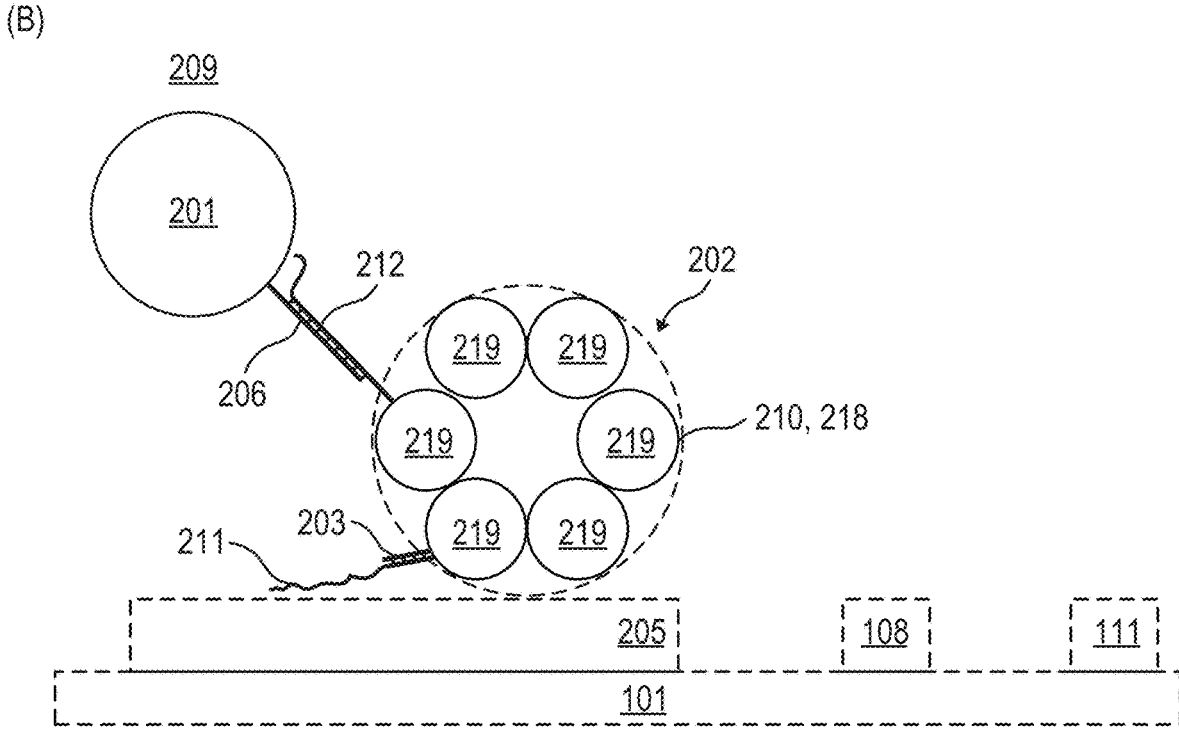
Figure 4:
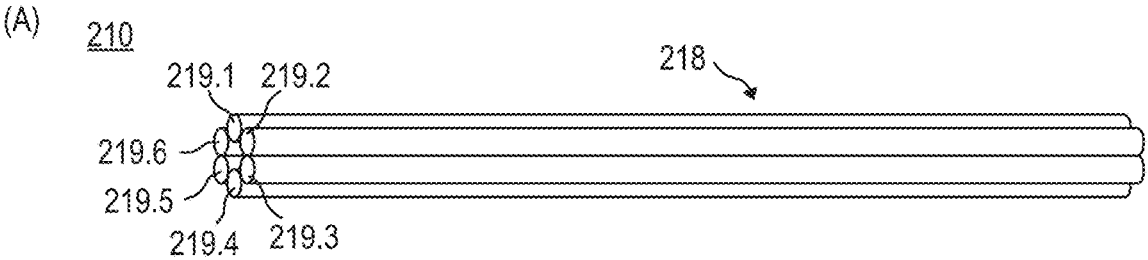
FIG. 4 shows, according to some embodiments: panel A) a perspective view of a nucleic acid core that includes a DNA helix bundle for six DNA helixes; (panel B) a side view of the nucleic acid core shown in panel A; (panel C) a cross-section along line A-A of the nucleic acid core shown in panel B; (panel D) a cross-section of a DNA helix bundle that includes ten DNA helixes arranged in a lemniscate configuration; and (panel E) cross-sections of various DNA helix bundles that includes different numbers of DNA helixes indicated by the number located centrally for each DNA helix bundle.
Figure 4:
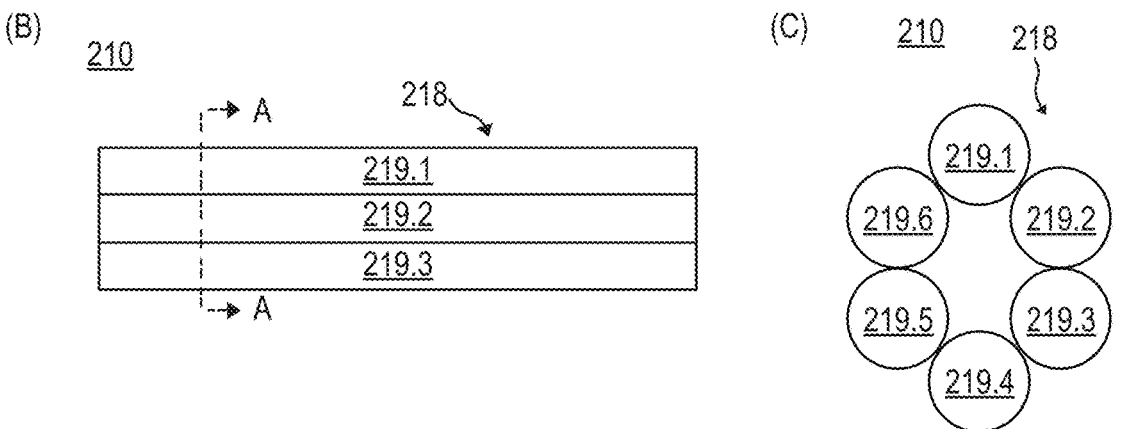
Figure 4:
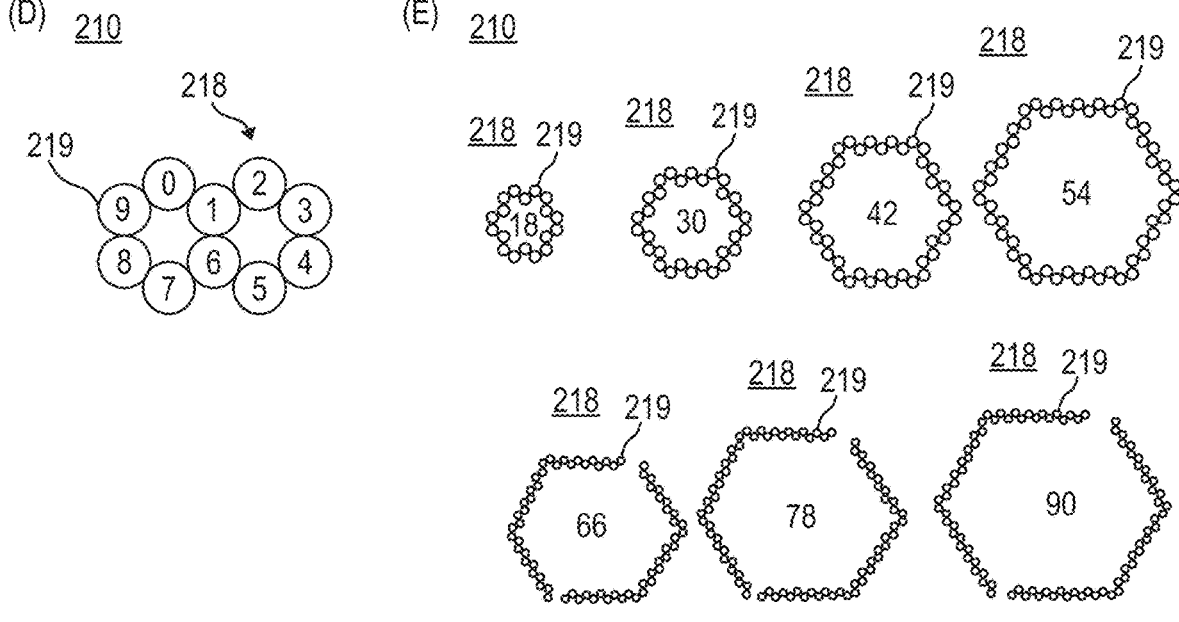
Figure 5:
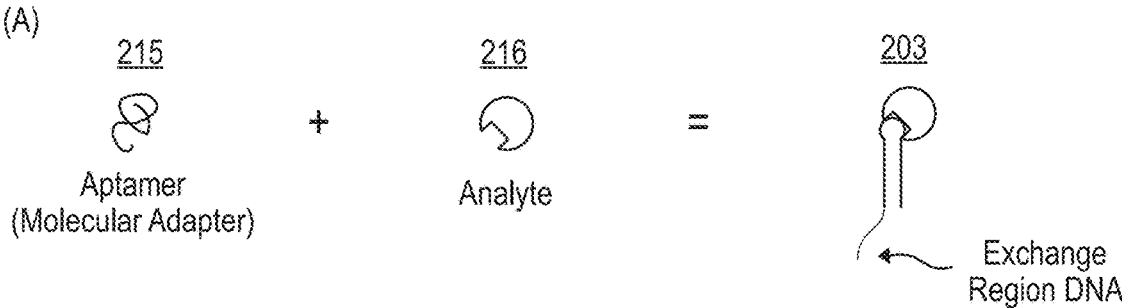
FIG. 5 shows, according to some embodiments: (panel A) formation of a chemical analyte from an aptamer and an analyte; (panel B) a DNA switch in a latched configuration wherein a second helix strand is hybridized to a first helix strand; and (panel C) the DNA switch in an unlatched configuration wherein the second helix strand is unhybridized to the first helix strand that is hybridized to the chemical analyte, wherein molecular adapters (e.g., aptamers) conjugate to probe DNA molecules that provide a variety of recognition elements.
Figure 5:
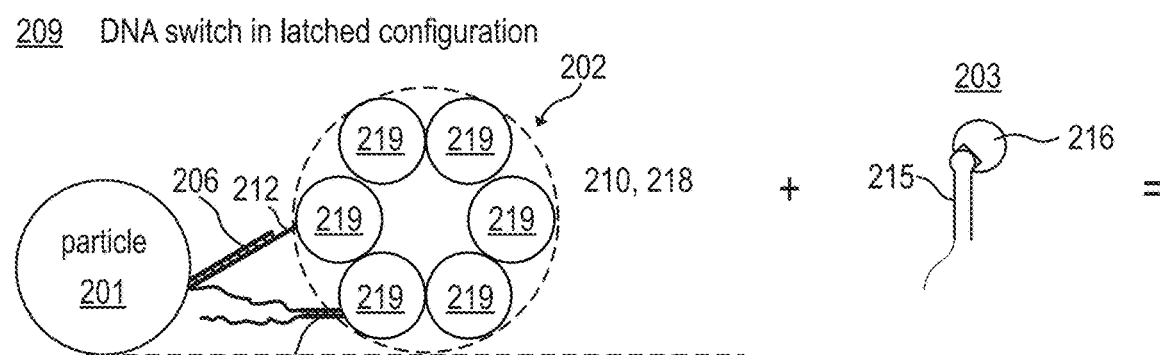
Figure 5:
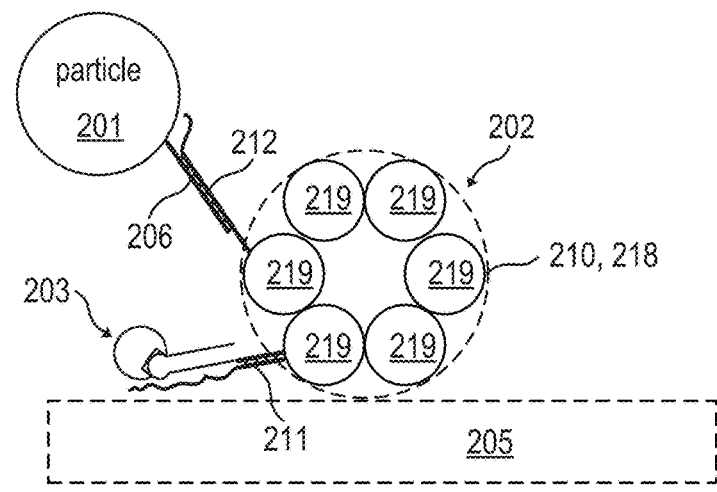

In an embodiment, with reference to FIG. 3, FIG. 4, and FIG. 5, DNA switch 209 includes: a DNA nanostructure framework 202 disposed on the analysis substrate 205 and including a nucleic acid core 210, a first helix strand 211 protruding from the nucleic acid core 210 and attached to the analysis substrate 205, and a second helix strand 212 protruding from the nucleic acid core 210 such that the second helix strand 212 is hybridized to the first helix strand 211 in an absence of a chemical analyte 203 that preferentially hybridizes to the first helix strand 211 as compared with the second helix strand 212, and the second helix strand 212 dissociates from the first helix strand 211 when the first helix strand 211 is in a presence of the chemical analyte 203; a particle strand 206 hybridized to the second helix strand 212; and a reporter particle 201 attached to the particle strand 206 and disposed proximate to the analysis substrate 205 when the second helix strand 212 is hybridized to the first helix strand 211 in absence of the chemical analyte 203 and that changes the electrical potential of the analysis substrate 205 depending on whether the second helix strand 212 is hybridized to the first helix strand 211.

In an embodiment, when the chemical analyte 203 is hybridized to the first helix strand 211, the reporter particle 201 remains attached to the nucleic acid core 210, and is sterically or thermodynamically precluded from interacting with first helix strand 211.

In an embodiment, the transduction member 114 includes a transimpedance amplifier 107. In some embodiment, the transduction member 114 further includes a transistor 105.

In an embodiment, agile nucleic acid sensor 200 includes a drain voltage source 106 in electrical communication with the transistor 105 and that produces a drain voltage 119 for the transistor 105.

In an embodiment, agile nucleic acid sensor 200 includes voltage setpoint source 110 in electrical communication with the voltage follower 109 and that produces the counter electrode voltage 117 for the voltage follower 109.

In an embodiment, agile nucleic acid sensor 200 includes a signal processor 103 in electrical communication with the transduction member 114 and that receives the transduction signal 116 from the transduction member 114.

In an embodiment, agile nucleic acid sensor 200 includes an interface pad 112 in electrical communication the transimpedance amplifier 107.

In an embodiment, agile nucleic acid sensor 200 includes a substrate 101 on which the DNA switch 209, the analysis substrate 205, the transduction member 114, the sensor counter electrode 108, the sensor reference electrode 111, and the voltage follower 109 are disposed.

In an embodiment, agile nucleic acid sensor 200 includes a plurality of agile nucleic acid sensors 200 arranged in array. In an embodiment, agile nucleic acid sensor 200 includes a signal processor 103, wherein, for each agile nucleic acid sensor 200, the signal processor 103 is in electrical communication with a transduction member 114, and the signal processor 103 receives a transduction signal 116 from the transduction member 114. In an embodiment, agile nucleic acid sensor 200 includes a plurality of interface pads 112, such that each transimpedance amplifier 107 is in electrical communication with an interface pad. In an embodiment, agile nucleic acid sensor 200 includes a substrate 101 on which the agile nucleic acid sensors 200 are disposed. In an embodiment, the agile nucleic acid sensors 200 individually include: a DNA switch 209 that contacts and selectively duplexes with a chemical analyte 203 comprising the biomarker; an analysis substrate 205 in electrostatic communication with the DNA switch 209 that is disposed on the analysis substrate 205, such that when the chemical analyte 203 duplexes with the DNA switch 209, the analysis substrate 205 produces a biomarker electrical signal 115; a transduction member 114 in electrical communication with the analysis substrate 205 and that receives the biomarker electrical signal 115 and produces a transduction signal 116 in response to receiving the biomarker electrical signal 115; a sensor counter electrode 108 in electrical communication with and capacitively coupled to the analysis substrate 205 and that receives a counter electrode voltage 117; a sensor reference electrode 111 in electrical communication and capacitively coupled to the analysis substrate 205 and that produces a feedback signal 118 based on electrical interactions with a composition that is in fluid contact with the feedback signal 118 and the analysis substrate 205; and a voltage follower 109 in electrical communication with the sensor counter electrode 108 and the sensor reference electrode 111 and that receives the feedback signal 118 from the sensor reference electrode 111 and produces the counter electrode voltage 117 for the sensor counter electrode 108 based on the feedback signal 118.

In an embodiment, the DNA switch 209 includes: a DNA nanostructure framework 202 disposed on the analysis substrate 205 and including a nucleic acid core 210, a first helix strand 211 protruding from the nucleic acid core 210 and attached to the analysis substrate 205, and a second helix strand 212 protruding from the nucleic acid core 210 such that the second helix strand 212 is hybridized to the first helix strand 211 in an absence of a chemical analyte 203 that preferentially hybridizes to the first helix strand 211 as compared with the second helix strand 212, and the second helix strand 212 dissociates from the first helix strand 211 when the first helix strand 211 is in a presence of the chemical analyte 203; a particle strand 206 hybridized to the second helix strand 212; and a reporter particle 201 attached to the particle strand 206 and disposed proximate to the analysis substrate 205 when the second helix strand 212 is hybridized to the first helix strand 211 in absence of the chemical analyte 203 and that changes the electrical potential of the analysis substrate 205 depending on whether the second helix strand 212 is hybridized to the first helix strand 211. In an embodiment, when the chemical analyte 203 is hybridized to the first helix strand 211: the reporter particle 201 remains attached to the nucleic acid core 210, and is sterically or thermodynamically precluded from interacting with first helix strand 211.

Various molecular structures described herein involve nucleic acids. As used herein, a "nucleic acid" can include deoxyribonucleic acid (DNA), ribonucleic acid (RNA), or artificial nucleic acids, such as a peptide nucleic acid (PNA). The molecular structure may include one type of nucleic acid (e.g., DNA), or more than one type in some cases, which may form part of the same molecule or different molecules assembled together in a supramolecular assembly defining the overall molecular structure. Typically, the nucleic acid is a polymeric molecule including one or more "bases" (usually nitrogenous) connected to a backbone structure, which can be a sugar-phosphate backbone (e.g., as in DNA or RNA) or a peptide backbone (e.g., as in PNA).

The sugars within the nucleic acid, when present, may be, for example, ribose sugars (as in RNA), or deoxyribose sugars (as in DNA). In some cases, the nucleic acid can include ribose and deoxyribose sugars. Examples of bases that may be found within a nucleic acid include, but are not limited to, the naturally-occurring bases (e.g., adenosine or "A," thymidine or "T," guanosine or "G," cytidine or "C," or uridine or "U"). The bases typically interact on a specific basis (i.e., guanosine interacts with cytidine via hydrogen bonding and vice versa, and adenosine interacts with thymidine or uridine via hydrogen bonding and vice versa). In some cases, the nucleic acid may include nucleoside analogs (e.g., 2-aminoadenosine, 2-thiothymidine, inosine, pyrrolopyrimidine, 3-methyladenosine, C5-bromouridine, C5-fluorouridine, C5-iodouridine, C5-propynyluridine, C5-propynylcytidine, C5-methylcytidine, 7-deazaadenosine, 7-deazaguanosine, 8-oxoadenosine, 8-oxoguanosine, 06-methylguanosine, 2-thiocytidine, 2-aminopurine, 2-amino-6-chloropurine, 2,6-diaminopurine, hypoxanthine), chemically or biologically modified bases (e.g., methylated bases), intercalated bases, modified sugars (2'-fluororibose, arabinose, or hexose), modified phosphate moieties (e.g., phosphorothioates or 5'-N-phosphoramidite linkages), or other naturally and non-naturally occurring bases substitutable into the nucleic acid, including substituted and unsubstituted aromatic moieties. Other suitable base or backbone modifications can occur.

The nucleic acid can be single-stranded or double-stranded, i.e., formed of two strands (or of the same strand looped back on itself, such as in a hairpin turn or a stem-loop structure) associated with each other via hydrogen bonding, e.g., via guanosine/cytidine base-pair interactions, adenosine/thymidine base-pair interactions, adenosine/uridine base-pair interactions, etc.

The nucleic acids can be present within a molecular structure as a bundle, which can include two or more non-complementary nucleic acid portions associated with each other. The nucleic acids forming the bundles can be single stranded or double stranded, and the non-complementary nucleic acid portions can be part of the same nucleic acid molecule or part of different nucleic acid molecules. For instance, there may be 2, 3, 4, 5, 6, 8, 10, 12, 14, 16, 18, 20, 24, 30, 42, 54, 66, 78, 90, or more non-complementary nucleic acid portions associated with each other as part of a bundle. There can be other nucleic acid strands associated with one or more portions of the nucleic acids forming the nucleic acid bundle, e.g., to provide stability.

It should be noted that, in a bundle of nucleic acid, not all of the nucleic acid strands need run from one end of the bundle to the other. For example, one or more nucleic acid strands may run from a first end of the bundle, through a hairpin turn or a stem-loop structure, back to the first end of the bundle (or may go through more than one hairpin turn or a stem-loop structure, in some cases); or a nucleic acid strand may end within the bundle.

In some cases, the bundles can define a nanotube. The nanotube can have a hollow center, with nucleic acid strands arranged around the center (thus, a double strand of DNA, by itself, is not a nanotube, as the two sugar-phosphate backbones forming the DNA are interconnected by bases hydrogen bonded to each other, which thus does not result in a hollow center). The nanotube may be circular or elliptical, or in some cases, the nanotube may have polygonal shapes such as a hexagon. In some cases, the nanotube may have more than one hollow center, e.g., having the shape of a lemniscate. Non-limiting examples of such nanotubes are shown in FIG. 3A (perspective view of a six-helix nucleic acid bundle), FIG. 3B (side view of the six-helix nucleic acid bundle shown in panel A), FIG. 3C (cross-section along line A-A of the six-helix nucleic acid bundle shown in panel B), FIG. 3D (a ten-helix nucleic acid bundle, having a lemniscate shape with two hollow centers; thus, more than one hollow center may be present within the nanotube), and FIG. 3E (bundles with the number of nucleic acid strands present within the nanotube shown in the center of each nanotube). The nucleic acid portions forming the bundled nanotube may be part of the same nucleic acid molecule or may be part of different nucleic acid molecules. In some cases, the nanotube may be formed from an even number of nucleic acid strands (e.g., 4, 6, 8, 10, 12, etc.). In certain embodiments, other molecules may be present within the nanotube, for example, to provide stability to the nanotube structure.

In some embodiments, one or more of the nucleic acid bundles or nanotubes within the molecular structure may be fabricated from one or more relatively long nucleic acids, e.g., having lengths of at least about 500 nucleotides, at least about 1,000 nucleotides, at least about 3,000 nucleotides, at least about 10,000 nucleotides, at least about 30,000 nucleotides, etc. Such a nucleic acid may be referred to as a nucleic acid scaffold. The nucleic acid scaffold may form a single bundle or nanotube, or may include different parts of different bundles or nanotubes in the final molecular structure. For instance, a nucleic acid scaffold may wrap in various ways around the molecular structure, e.g., forming various nucleic acid bundles or nanotubes defining the molecular structure. In some cases, a nucleic acid may form a first portion of a nucleic acid bundle and a second portion of the same nucleic acid bundle (or a different one), where the first and second portions forming the nucleic acid bundle are not complementary. In one set of embodiments, the nucleic acid scaffolds are substantially free of self-complementary regions and/or repeat units, as discussed below. In certain embodiments of the invention, the nucleic acid scaffolds are immobilized to form one or more bundles or nanotubes, and ultimately a three-dimensional structure, using one or more nucleic acid stabilizers able to associate with two or more portions of the nucleic acid. In certain embodiments, the structures can have other shapes, e.g., notched rectangles, as well as other planar or three-dimensional structures.

One source of a nucleic acid having such characteristics is bacteriophage DNA, for example, M13 bacteriophage. The DNA in such bacteriophages may be single stranded DNA, and have substantially few self-complementary regions (e.g., only 2 hairpin regions may form), and a length of about 7,000 nucleotides. The DNA can be removed from the bacteriophage using DNA isolation techniques known to those of ordinary skill in the art, for example, by using lysis buffer (e.g., comprising an alkaline environment or surfactant) followed by centrifugation at greater than 10,000 RCF (relative centrifugal force) to separate the DNA.

The molecular structure may be stabilized, in some cases, by nucleic acid stabilizers able to associate with two or more nucleic acid portions. For example, a nucleic acid stabilizer may include a first portion complementary to a first nucleic acid strand (e.g., a nucleic acid scaffold) and a second portion complementary to a second nucleic acid strand. The first and second portions may be part of the same nucleic acid molecule, or may be part of different molecules. In some cases, the nucleic acid stabilizer may be formed essentially from nucleic acid. A nucleic acid stabilizer may have a length of between about 20 nucleotides and about 100 nucleotides, for example, between about 35 nucleotides and about 45 nucleotides, or about 40 nucleotides. As the first portion of the nucleic acid stabilizer binds to the first nucleic acid portion and the second portion binds to the second nucleic acid portions, the two portions are substantially immobilized, relative to each other, due to the presence of the nucleic acid stabilizer. Thus, the two portions are not able to move apart, or at least are not able to move far apart, and remain associated together. By using a plurality of nucleic acid stabilizers, e.g., targeted to different nucleic acids or different portions of nucleic acids, one or more nucleic acids can be stabilized in a substantially rigid configuration, e.g., as a bundle or a nanotube. In addition, these can further be configured as part of larger molecular structures. A technique for forming nucleic acid stabilizers is found in Rothemund, P. W. K., "Folding DNA to Create Nanoscale Shapes and Patterns," *Nature,* 440:297-302 (2006), which is incorporated by reference in its entirety.

As used herein, "microRNA" or "miRNA" describes small, non-coding RNA molecules, generally about 15 to about 50 nucleotides in length, specifically 17-23 nucleotides, that can play a role in regulating gene expression through, e.g., a process referred to as RNA interference (RNAi). RNAi describes a phenomenon whereby the presence of an RNA sequence that is complementary or anti-sense to a sequence in a target gene messenger RNA (mRNA) results in inhibition of expression of the target gene. Here, miRNAs are processed from hairpin precursors of about 70 or more nucleotides (pre-miRNA) that are derived from primary transcripts (pri-miRNA) through sequential cleavage by RNAse III enzymes. Moreover, miRBase is a comprehensive microRNA database located at www.mirbase.org, incorporated by reference herein in its entirety for all purposes.

The RNAi can be transcribed as an RNA precursor having a hairpin-like structure, cleaved by a dsRNA-cleaving enzyme having RNase III cleavage activity, and integrated into a protein complex called RISC and can be involved in the suppression of translation of mRNA. The term "miRNA" includes not only a "miRNA" represented by a particular nucleotide sequence but a "miRNA" including a precursor of the "miRNA" (pre-miRNA or pri-miRNA) and having biological functions equivalent to miRNAs encoded by these, e.g., a "miRNA" encoding a congener (i.e., a homolog or an ortholog), a variant such as a genetic polymorph, and a derivative. Such a "miRNA" encoding a precursor, a congener, a variant, or a derivative can be specifically identified using miRBase Release 22 (http://www.mirbase-.org/), and examples thereof can include a "miRNA" having a nucleotide sequence hybridizing to a complementary nucleotide sequence. It is contemplated that miRNA can be a gene product of a miR gene. Such a gene product includes a mature miRNA (e.g., a 15- to 25-nucleotide or 19- to 25-nucleotide non-coding RNA involved in the suppression of translation of mRNA as described above) or a miRNA precursor (e.g., pre-miRNA or pri-miRNA as described above).

Complementary polynucleotide and similar referents such as complementary strand or reverse strand includes a polynucleotidee in a complementary relationship based on A:T (U) and G:C base pairs with the full-length sequence of a polynucleotide or a nucleotide sequence derived from the nucleotide sequence by the replacement of U with T, or a partial sequence thereof (here, this full-length or partial sequence is referred to as a plus strand for the sake of convenience). However, such a complementary strand is not limited to a sequence completely complementary to the nucleotide sequence of the target plus strand and may have a complementary relationship to an extent that permits hybridization under stringent conditions to the target plus strand.

The term "$T_m$ value" refers to a temperature at which the double-stranded moiety of a polynucleotide is denatured into single strands so that the double strands and the single strands exist at a ratio of 1:1.

The term "aptamer" indicates oligonucleic acid or peptide molecules that are capable to bind a specific target. It is contemplated that the aptamer can include single-stranded oligonucleotides and chemically synthesized peptides that have been engineered through repeated rounds of in vitro selection, or equivalent techniques identifiable by a skilled person, to bind to various targets.

As used herein, the term "nucleotide" refers to a molecule that includes a sugar and at least one phosphate group, and optionally also includes a nucleobase. A nucleotide that lacks a nucleobase can be referred to as "abasic." Nucleotides include deoxyribonucleotides, modified deoxyribonucleotides, ribonucleotides, modified ribonucleotides, peptide nucleotides, modified peptide nucleotides, modified phosphate sugar backbone nucleotides, and mixtures thereof. Examples of nucleotides include adenosine monophosphate (AMP), adenosine diphosphate (ADP), adenosine triphosphate (ATP), thymidine monophosphate (TMP), thymidine diphosphate (TDP), thymidine triphosphate (TTP), cytidine monophosphate (CMP), cytidine diphosphate (CDP), cytidine triphosphate (CTP), guanosine monophosphate (GMP), guanosine diphosphate (GDP), guanosine triphosphate (GTP), uridine monophosphate (UMP), uridine diphosphate (UDP), uridine triphosphate (UTP), deoxyadenosine monophosphate (dAMP), deoxyadenosine diphosphate (dADP), deoxyadenosine triphosphate (dATP), deoxythymidine monophosphate (dTMP), deoxythymidine diphosphate (dTDP), deoxythymidine triphosphate (dTTP), deoxycytidine diphosphate (dCDP), deoxycytidine triphosphate (dCTP), deoxyguanosine monophosphate (dGMP), deoxyguanosine diphosphate (dGDP), deoxyguanosine triphosphate (dGTP), deoxyuridine monophosphate (dUMP), deoxyuridine diphosphate (dUDP), and deoxyuridine triphosphate (dUTP).

The term "nucleotide" also include any "nucleotide analogue which is a type of nucleotide that includes a modified nucleobase, sugar or phosphate moiety compared to naturally occurring nucleotides. Exemplary modified nucleobases that can be included in a polynucleotide, whether having a native backbone or analogue structure, include, inosine, xathanine, hypoxathanine, isocytosine, isoguanine, 2-aminopurine, 5-methylcytosine, 5-hydroxymethyl cytosine, 2-aminoadenine, 6-methyl adenine, 6-methyl guanine, 2-propyl guanine, 2-propyl adenine, 2-thiouracil, 2-thiothymine, 2-thiocytosine, 15-halouracil, 15-halocytosine, 5-propynyl uracil, 5-propynyl cytosine, 6-azo uracil, 6-azo cytosine, 6-azo thymine, 5-uracil, 4-thiouracil, 8-halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7-methylguanine, 7-methyladenine, 8-azaguanine, 8-azaadenine, 7-deazaguanine, 7-deazaadenine, 3-deazaguanine, 3-deazaadenine or the like. As is known in the art, certain nucleotide analogues cannot become incorporated into a polynucleotide, for example, nucleotide analogues such as adenosine 5'-phosphosulfate.

As used herein, the term "polynucleotide" refers to a molecule that includes a sequence of nucleotides that are bonded to one another. Examples of polynucleotides include deoxyribonucleic acid (DNA), ribonucleic acid (RNA), and analogues thereof. A polynucleotide can be a single stranded sequence of nucleotides, such as RNA or single stranded DNA, a double stranded sequence of nucleotides, such as double stranded DNA, or can include a mixture of a single stranded and double stranded sequences of nucleotides. Double stranded DNA (dsDNA) includes genomic DNA, and PCR and amplification products. Single stranded DNA (ssDNA) can be converted to dsDNA and vice-versa. The precise sequence of nucleotides in a polynucleotide can be known or unknown. The following are exemplary examples of polynucleotides: a gene or gene fragment (for example, a probe, primer, expressed sequence tag (EST) or serial analysis of gene expression (SAGE) tag), genomic DNA, genomic DNA fragment, exon, intron, messenger RNA (mRNA), transfer RNA, ribosomal RNA, ribozyme, cDNA, recombinant polynucleotide, synthetic polynucleotide, branched polynucleotide, plasmid, vector, isolated DNA of any sequence, isolated RNA of any sequence, nucleic acid probe, primer or amplified copy of any of the foregoing.

As used herein, "hybridize" refers to noncovalently binding a first polynucleotide to a second polynucleotide. The strength of the binding between the first and second polynucleotides increases with the complementarity between those polynucleotides.

As used herein, the term "protein" refers to a molecule that includes a polypeptide that is folded into a three-dimensional structure. The polypeptide includes moieties that, when folded into the three-dimensional structure, impart the protein with biological activity.

The term "sensor" indicates a device that measures a physical quantity and converts it into a signal which can be read by an observer or by an instrument. The sensors can be calibrated against a known standard.

The term "detect" or "detection" indicates determination of the existence or presence of a chemical analyte or other target or signal in a limited portion of space, including but not limited to a sample, a reaction mixture, a molecular complex and a substrate including a platform and an array. Detection is "quantitative" when it refers, relates to, or involves the measurement of quantity or amount of chemical analyte or signal (also referred as quantification), which includes but is not limited to any analysis designed to determine the amounts or proportions of the chemical analyte or signal. Detection is "qualitative" when it refers, relates to, or involves identification of a quality or kind of the chemical analyte or signal in terms of relative abundance to another chemical analyte or signal, which is not quantified. An "optical detection" indicates detection performed through visually detectable signals: spectra or images from a chemical analyte or a probe attached to the chemical analyte. An "electrical detection" indicates detection performed through electrically detectable signals: voltage, electrical current, induction, or capacitance from a chemical analyte or a probe attached to the chemical analyte.

The term "chemical analyte" refers to a substance, compound, or component whose presence or absence in a sample is detected through hybridization. Chemical analytes include biomolecules and in particular biomarkers. The term "biomolecule" indicates a substance compound or component associated to a biological environment including but not limited to sugars, amino acids, peptides proteins, oligonucleotides, polynucleotides, polypeptides, organic molecules, haptens, epitopes, biological cells, parts of biological cells, vitamins, hormones, and the like. The term "biomarker" indicates a biomolecule that is associated with a specific state of a biological environment including but not limited to a phase of cellular cycle, health, and disease state. The presence, absence, reduction, upregulation of the biomarker is associated with and is indicative of a particular state. The term "biological environment" refers to any biological setting, including, for example, ecosystems, orders, families, genera, species, subspecies, organisms, tissues, cells, viruses, organelles, cellular substructures, prions, and samples of biological origin. Exemplary chemical analytes include molecular targets such as small molecules, proteins, nucleic acids, and also cells, tissues, and organisms.

The term "spectroscopic probe" indicates a substance that is suitable to be detected based on an interaction between a radiation and the substance through a spectroscopic instrument. Exemplary spectroscopic probes comprise Raman probes and fluorescence probes. The terms "Raman active molecule" or "Raman probe" as used herein refer to a molecule capable having a polarization-dependent vibrational mode excited by an incident light. The vibrational energy stored in the molecule is transformed into a scattering light corresponding to a specific frequency. In particular, detected signals emitted by Raman probes can take the form of Raman spectra. Accordingly, in Raman spectra for a certain Raman probe, each peak represents the vibrational frequency corresponding to resonance energy of the functional groups in the Raman probe as detected. Therefore, Raman spectra are intrinsic properties of the molecules such as a "molecular fingerprint" to identify the molecule without need to use of any additional labels.

In some embodiments, Raman probes suitable to be included in the chemical analyte include Raman-active molecules having polarization-dependent rotational modes. Exemplary Raman probes suitable to be used in the chemical analyte include trans-1,2 bis-(4-pyridyl) ethylene (BPE), Cy-3, Cy-3.5, Cy-5, Cy-5.5, Cy-7, Rhodamine 6G (R6G), methylene blue (MB), 5-carboxyfluorescein or 6-carboxyfluorescein (FAM), N,N,N',N'-tetramethyl-6-carboxy-rhodamine (TAMRA), 6-carboxy-4,7,2',7'-tetrachlorofluorescein (TET), 6-carboxy-Xrhodamine (ROX), (3-(5,6,4',7'-tetrachloro-5'-methyl-3',6'-dipivaloylfluorescein-2-yl)-propanamidohexyl-1-O-(2-cyanoethyl)-(N,N-diisopropyl)) Yakima Yellow®, 6-(((4(4,4-difluoro-5-(2-thienyl)-4-bora-3a,4a-diaza-s-indacene-3-yl)phenoxy)acetyl)amino) hexanoic acid (BODIPY TR-X) and additional probes identifiable by a skilled person upon reading of the present disclosure.

The term "fluorescent probe" indicates a substance that is detectable through emission of a visible light by the substance following absorption by the same substance of light of a differing, usually nonvisible, wavelength. Exemplary fluorescent probes suitable in the chemical analyte include Cy-3, Cy-3.5, Cy-5, Cy-5.5, Cy-7, Rhodamine 6G (R6G), methylene blue (MB), TAMRA, and additional probes identifiable by a skilled person.

The term "attach" or "attached" refers to connecting or uniting by a bond or other link or force that keeps two or more components together, which encompasses either direct or indirect attachment where, for example, a first molecule is directly bound to a second molecule or material, or one or more intermediate molecules are disposed between the first molecule and the second molecule or material. The term "bind", "binding", and "conjugation" indicates an attractive interaction between two elements that results in a stable association of the elements in which the elements are in close proximity to each other. Attractive interactions include both non-covalent binding and covalent binding. Non-covalent binding indicates a type of chemical bond, such as protein-protein interaction, that does not involve the sharing of pairs of electrons, but rather involves more dispersed variations of electromagnetic interactions. Non-covalent bonding includes ionic bonds, hydrophobic interactions, electrostatic interactions, hydrogen bonds, and dipole-dipole bonds. Electrostatic interactions include association between two oppositely charged entities.

According to an exemplary embodiment, spectroscopic probes, such as methylene blue, can be attached to the chemical analyte formed by an oligonucleotide through active ester coupling to an amine group (e.g. a 3' C7 amine of an oligonucleotide aptamer).

In some embodiments, a spectroscopic probe, and in particular a Raman probe, can be attached to the chemical analyte by a covalent bond, with or without one or more intermediate molecules, to any position where attachment does not interfere with binding to the aptamer or hybridization to the chemical analyte.

The wording "specific" or "specificity" with reference to hybridization or binding of the chemical analyte or generally of a first molecule to a second molecule refers to the recognition, contact, and formation of a stable complex between the first molecule and the second molecule, together with substantially less to no recognition, contact and formation of a stable complex between each of the first molecule and the second molecule with other molecules that may be present. Exemplary specific bindings include polynucleotide hybridization. The term "specific" as used herein with reference to a sequence of a polynucleotide refers to the unique association of the sequence with a single polynucleotide which is the complementary sequence.

In some embodiment, a nucleic acid core of a DNA switch is immobilized through electrostatic forces to a suitable substrate so that the spectroscopic probe attached to chemical analyte is likewise immobilized to the nucleic acid core proximate to the substrate.

In several embodiments, DNA switch 209 or biomarker signal amplifier 208 herein described can detect chemical analytes with a high sensitivity showing a limit of detection≤100 pM and more particularly within a dynamic range spanning from about 100 pM to about 1 pM depending on the assay performed.

In several embodiments, DNA switch 209 or biomarker signal amplifier 208 can detect chemical analytes with high specificity, wherein the selective hybridization of the chemical analyte to DNA switch 209 or biomarker signal amplifier 208 over other analytes can be shown by specific discrimination of the chemical analyte via electrical detection or optical detection.

In an embodiment, reporter particle 201 includes a nanoparticle, a quantum dot, a charged polymer, or a combination thereof. The nanoparticle of reporter particle 201 can include a gold nanoparticle. The nanoparticle of reporter particle 201 can have a surface charge.

In an embodiment, reporter particle 201 includes a spectroscopic probe such as a fluorophore, Raman probe, or the like disposed on a nanoparticle.

In an embodiment, chemical analyte 203 includes a nucleic acid, DNA, RNA, or a combination thereof. According to an embodiment, with reference to FIG. 8, chemical analyte 203 includes aptamer 215 and analyte 216. The analyte can include a spectroscopic probe, chemical functional group, and the like.

In an embodiment, surface strand 204 includes single stranded DNA.

In an embodiment, particle strand 206 includes a base sequence that is complementary to the single stranded DNA of the surface strand 204.

In an embodiment, analysis substrate 205 includes a metal, a glass, a ceramic, or a combination thereof on which the other components of biomarker signal amplifier 208 or DNA switch 209 can be disposed.

In an embodiment of DNA switch 209, when chemical analyte 203 is hybridized to first helix strand 211, reporter particle 201 remains attached to nucleic acid core 210 and is sterically or thermodynamically precluded from interacting with first helix strand 211.

In an embodiment, DNA nanostructure framework 202 includes a 2D nanostructure. Exemplary 2D nanostructures include wireframes of polynucleotides, DNA origami, and the like such as 2D arrays.

In an embodiment, DNA nanostructure framework 202 includes a 3D nanostructure. Exemplary 2D nanostructures include wireframes of polynucleotides, DNA origami, and the like such as polyhedral, bundles, and the like. According to an embodiment, DNA nanostructure framework 202 is a DNA backbone helix.

Elements of DNA nanotechnology-based biomarker measurement platform 200 and its components can be various sizes and can be varied by a choice of materials.

It is contemplated that large nanoparticles (e.g., with large surface charge or decorated with fluorophores and the like) integrated within a DNA nanostructure framework amplify electrical signal generated in presence of a chemical analyte. With reference to FIG. 1, a single-stranded DNA as surface strand 204 is attached to a surface of analysis substrate 205 (e.g., gold, silica, and the like etc.) using a chemical attachment (e.g., thiol chemistry, silane chemistry, and the like). Reporter particle 201 (e.g., gold nanoparticle, quantum dot, large charged polymer, and the like) with a complementary DNA strand as particle strand 206 is hybridized with surface strand 204 to attach reporter particle 201 in proximate to the surface of analysis substrate 205. The ability to use DNA nanostructures to confine reporter particle 201 proximate to the surface provides a sensitive detection modality such as electronic detection via an electronic signal.

Regarding DNA switch 209, for robust signal amplification, DNA switch 209 provides selective rather than nonspecific binding of chemical analyte 203 (e.g., from unintended interactions between released reporter particle 201 and analysis substrate 205) that could otherwise result in erroneous kinetics measurement. DNA switch 209 minimizes non-specific interactions with chemical analyte 203. While the configuration shown in FIG. 2 include DNA helix bundle 218 as nucleic acid core 210, nucleic acid core 210 is not limited to just DNA helix bundle 218. Indeed, a variety of 2D and 3D DNA nanostructures for nucleic acid core 210 supports functions of DNA switch 209 described here.

Figure 2:
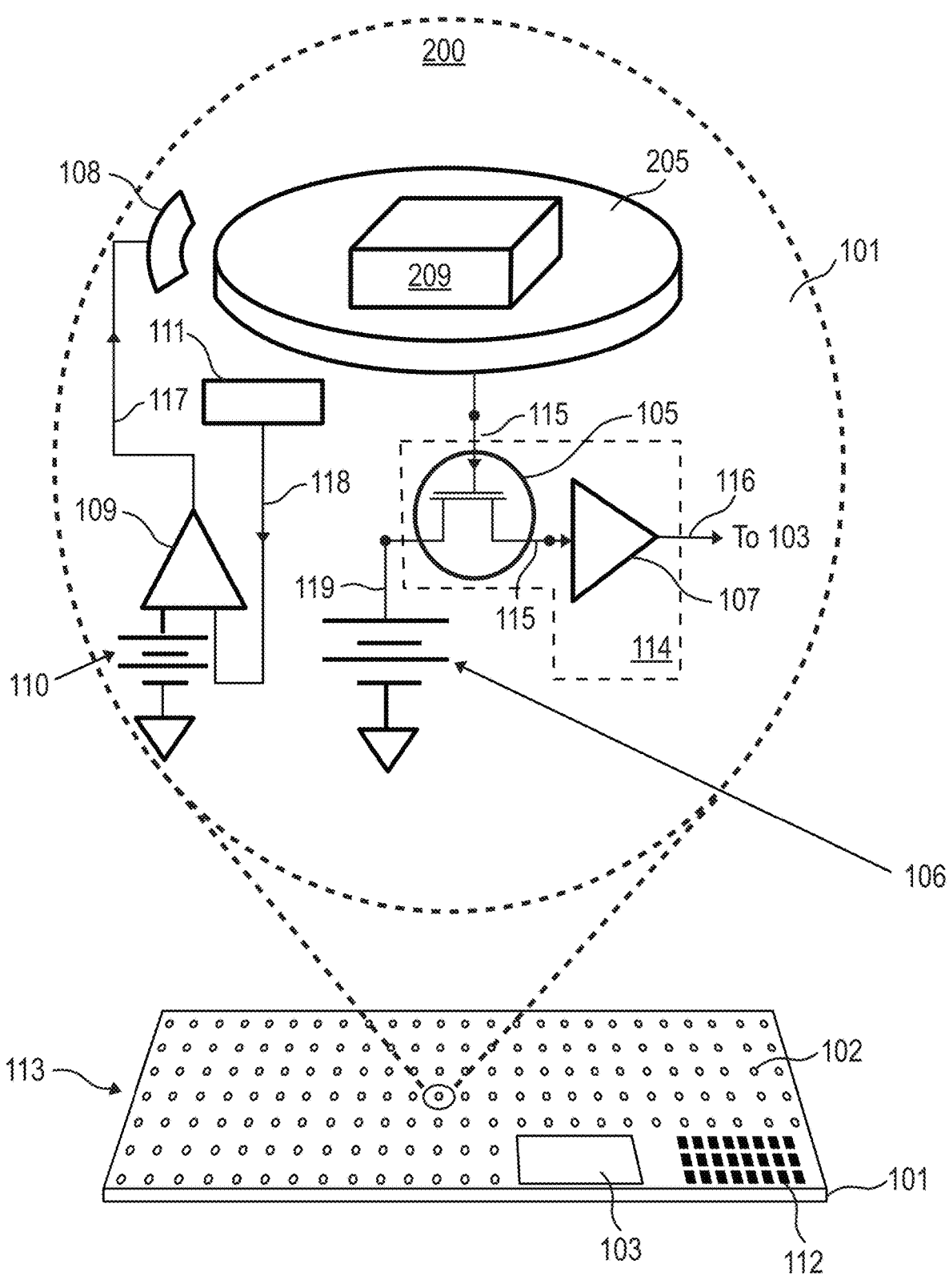
FIG. 2 shows an agile nucleic acid sensor, according to some embodiments.

In the configuration shown in FIG. 2, nucleic acid core 210 is assembled with reporter particle 201 including particle strand 206 that can be a DNA strand hybridized with both second helix strand 212 and first helix strand 211. This configuration can restrict reporter particle 201 to be proximate to the surface of analysis substrate 205 where reporter particle 201 can be detected using a sensing approaches discussed below. Upon addition of chemical analyte 203, which preferentially binds first helix strand 211 with the strand displacement shown in panel B of FIG. 1, reporter particle 201 is displaced from being proximate to analysis substrate 205 and moves distally away from analysis substrate 205 as shown in panel B of FIG. 2, indicating bound chemical analyte 203. Advantageously, when chemical analyte 203 is bound by DNA switch 209 through hybridization not first helix strand 211, reporter particle 201 is still constrained to DNA helix bundle 218 of nucleic acid core 210. Furthermore, reporter particle 201 is sterically and thermodynamically precluded from interacting with first helix strand 211, minimizing any non-specific interactions with analysis substrate 205.

In an embodiment, DNA switch 209 has tunable sensitivity toward chemical analyte 203. As unlatching of reporter particle 201 from analysis substrate 205 is mediated by binding competition between second helix strand 212 and chemical analyte 203 binding for first helix strand 211 sequence, the sensitivity of the displacement of reporter particle 201 with respect to analysis substrate 205 can be tuned by changing the predetermined second helix strand 212/first helix strand 211 affinity via sequence length. This tuning can simultaneously modify the thermodynamics (ultimate binding affinity) and kinetics (binding rate) with respect to chemical analyte 203. As thermodynamics and kinetics can be measured from the same signal readout, and they can be characterized for chemical analyte 203 to provide an internal consistency check for detection of chemical analyte 203.

With regard to the signal readout, biomarker signal amplifier 208 and DNA switch 209 are compatible with multiple readout methods that include but are not limited to the following techniques. When reporter particle 201 with a large surface charge is used (e.g., Au nanoparticles with a high surface coverage of DNA, and the like) with analysis substrate 205 that is connected to a charge sensitive electronic readout system (e.g., field-effect transistors, amplifiers, and the like), a large change in the surface potential at the input of the electronics interface results that is easily detected. Exemplary readout systems are described in U.S. patent application Ser. Nos. 16/220,866, 16/867,590, and 17/029,999, the disclosures of which are incorporated herein by reference in their entirety.

Signals output by each readout approach can be processed to extract information about the type or concentration of chemical analyte 203. Because biomarker signal amplifier 208 and DNA switch 209 leverages nanoscale features of DNA constructs, such can be formatted into a sensor array to simultaneously measure a spatial distribution of chemical analytes 203 that can be suited for processing with the pattern recognition capabilities of artificial intelligence (AI) or machine learning (ML) algorithms. Such approaches include but are not limited to deep neural networks (DNNs), neuromorphic elements, or other software or hardware components.

Figure 8:
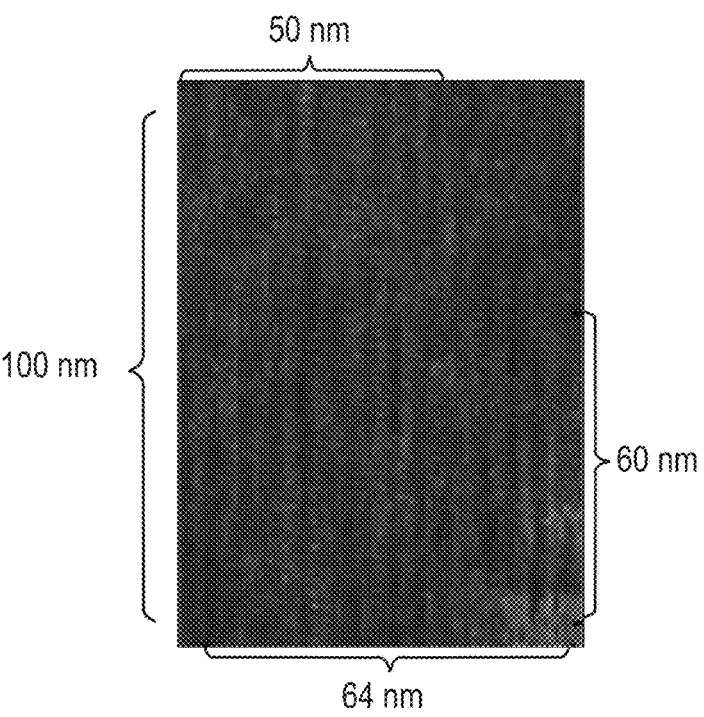
FIG. 8 shows a notched rectangle origami for sensing a biomarker, according to some embodiments.
Figure 8:
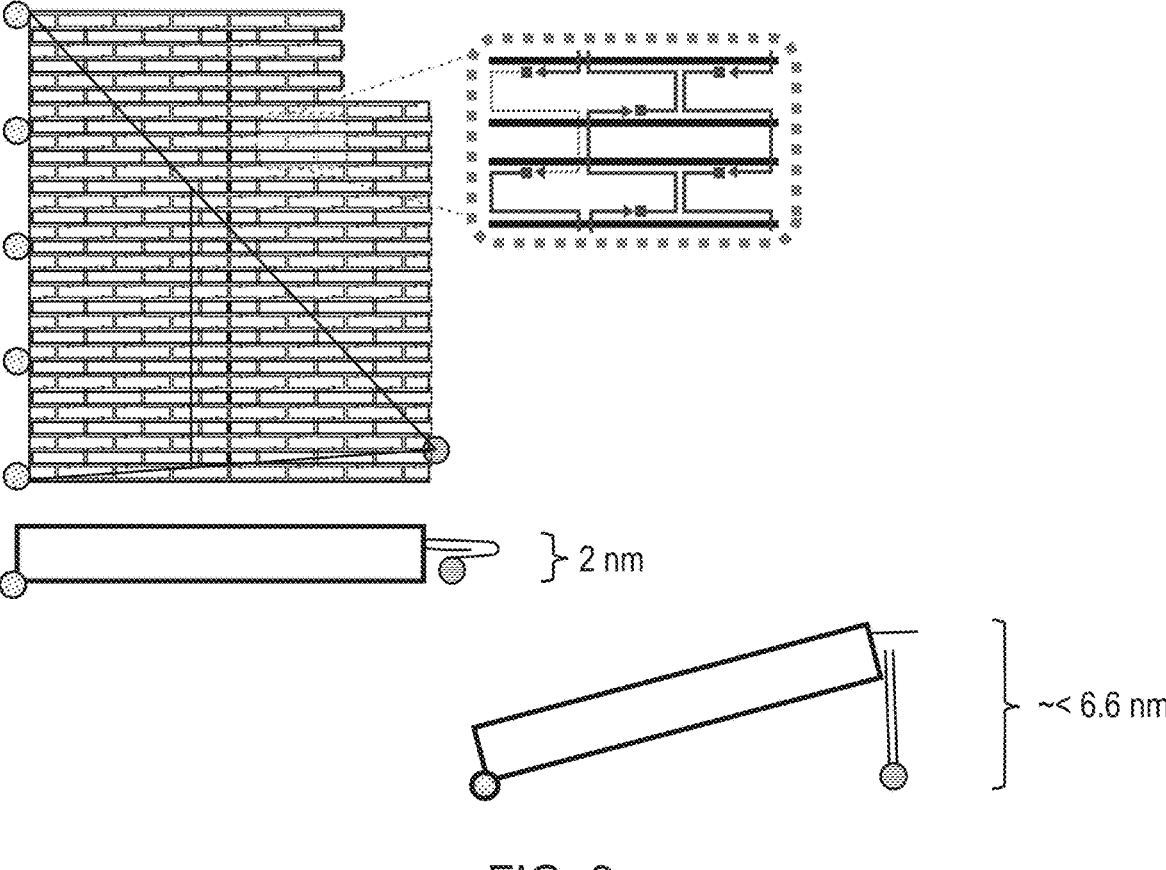

In an embodiment, chemical analyte 203, biomarker signal amplifier 208, or DNA switch 209 can include a molecular adapter, e.g., chemical analyte 203 as shown in FIG. 8. Molecular adapters can be, e.g., an aptamer, antibody, protein, and the like that can be conjugated to probe DNA strands for recognition of various target analytes, e.g., analyte 216, in solution to form chemical analyte 203. FIG. 8 shows aptamer 215 that captures target analyte 216 in solution and forms chemical analyte 203. When analyte 216 is bound to aptamer 215, aptamer 215 changes conformation to provide aptamer exchange region 220 to be activated. The DNA probe strands (e.g., aptamer exchange region 220) attached to aptamer 215 in chemical analyte 203 interact with sites (e.g., first helix strand 211) on DNA helix bundle 218 of nucleic acid core 210 to displace reporter particle 201. This modular approach provides DNA nanotechnology-based biomarker measurement platform 200 to rapidly adapt to particular applications. DNA nanotechnology-based biomarker measurement platform 200 with aptamer 215-based chemical analyte 203 also allows commonly used approaches such as sandwich antibody assays to be adapted for use with advances in biotechnology.

Figure 9:
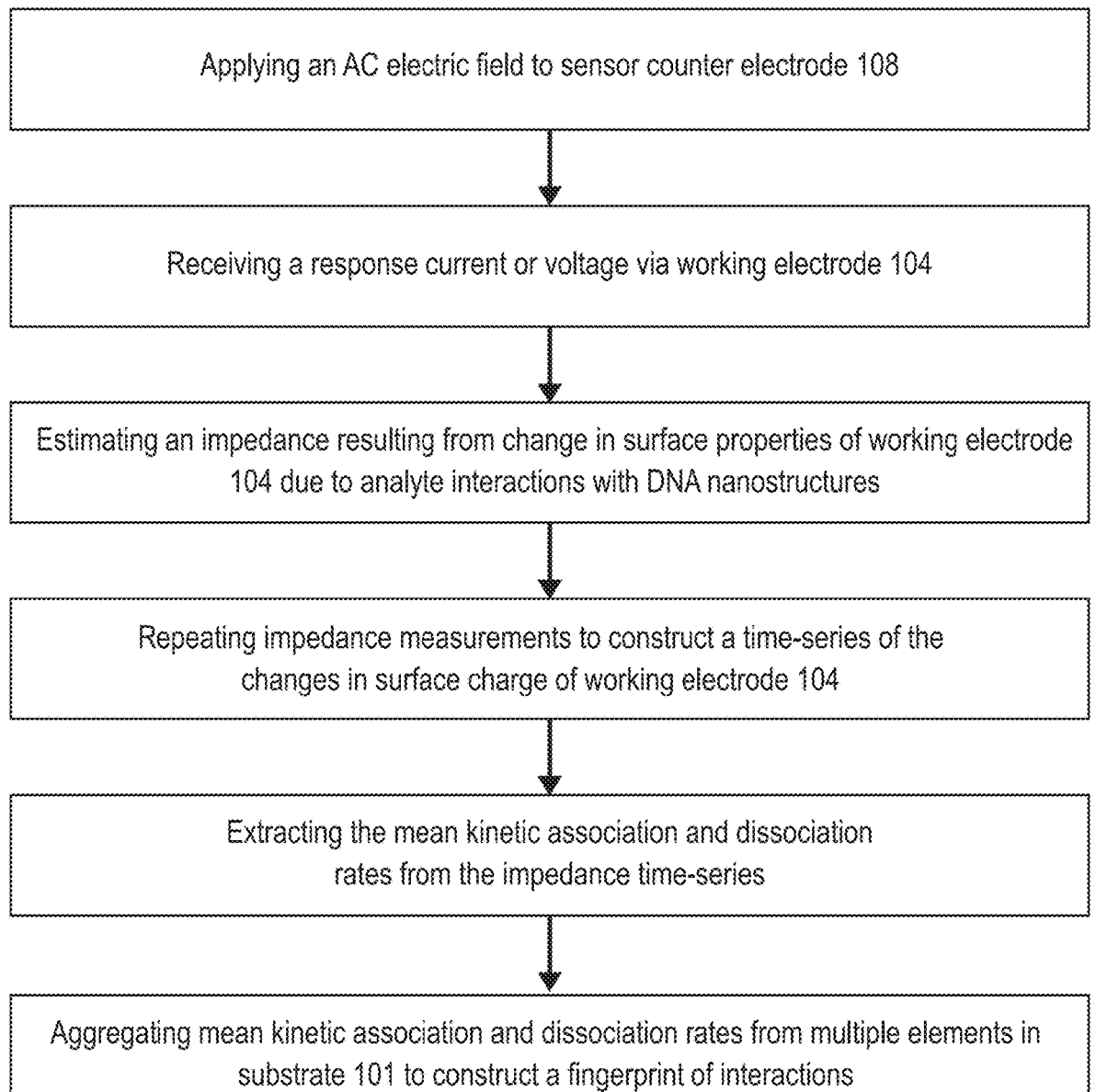
FIG. 9 shows steps in measuring a biomarker with an agile nucleic acid sensor, according to some embodiments.

Regarding DNA amplifier gain, resolution, and dynamic range, the gain of biomarker signal amplifier 208 or DNA switch 209 can be precisely defined by engineering the properties of reporter particle 201 (e.g., using geometry, surface charge, fluorophore density, and the like). FIG. 9 shows DNA nanotechnology-based biomarker measurement platform 200 that operates as a multi-chemical analyte sensor with a variable gain at each interaction site 209.$k$, defined by the size and charge of individual reporter particles 201. Each analyte binding site of DNA switch 209.$k$ is designed to bind a different type of chemical analyte 203. All binding sites 209 are read with a single electronic detector. When chemical analytes 203 bind to the individual sites 209.$k$ at individual first helix strand 211, the change in the signal (shown in FIG. 9 as AA, AB, AC, and the like) are proportional to the size and charge on the respective reporter particle 201, e.g., particle A, B, C, and the like. When the electronic detector has single particle resolution, the detection of binding events allows determination of the specific site 209 that was activated and therefore the type of chemical analyte 203.

DNA nanotechnology-based biomarker measurement platform 200 provides a one-to-one correspondence between the detection of chemical analyte 203 and its amplification through displacement of reporter particle 201 from analysis substrate 205. The resolution of the measurement is determined by the sensitivity of the detection technique to reporter particle 201. As an example, electrostatic interfacial potential $\zeta$ of a hydrated nanoparticle covered with DNA strands is tens of millivolts so that single molecule discrimination of reporter particles 201 and single molecule detection of bound chemical analyte 203 can be performed. A similar resolution is obtained by using optical and other imaging techniques to measure reporter particles 201 such as fluorescent nanoparticles, quantum dots and the like.

It is contemplated that agile nucleic acid sensor array 113 with agile nucleic acid sensors 200 can be configured in various manners. In an embodiment, substrate 101 supports the CMOS circuitry in n contact with a pixel element 102. The pixel element 102 includes sensor working electrode 104 made from a conductive material in electrical contact with the gate of a transistor 105 and in electrical contact with fluid surrounding the pixel. The transistor is powered by a drain voltage source 106, and the current in the channel is interrogated using a transimpedance amplifier 107. Here, the output of the transistor is communicated electrically to signal processor 103 that includes analog to digital converters, multiplexers and memory registers to configure the measurements. The pixel element 102 also can include a sensor working electrode 108 that is biased by voltage follower 109 and is in electrical contact with fluid surrounding the pixel. The voltage follower 109 can be biased by a voltage set-point source 110 and a sensor reference electrode 108 that provide a chemical reference that is in electrical contact with fluid surrounding the pixel.

In some embodiments, transimpedance amplifier 201 is a readout for sensor working electrode 205 and is in electrical communication with signal processing element 103 in an absence of transistor 105.

Sensor working electrode 205 can be functionalized with chemical species that control its behavior and allow the measurements of chemical analytes. In an embodiment, agile nucleic acid sensor 200 includes working electrode 205 in contact with a DNA switch 209 and that supports first helix strand 211 made from a DNA sequence, an aptamer or other suitable molecular adapter; reporter particle 201 including gold particles covered in DNA, DNA nanostructures or other structures constructed from charged species to amplify movement of reporter particle 201 closer to or further away from analysis substrate 205. In an analyte off configuration (FIG. 3A), reporter particle 201 is held in place by first helix strand 211. In the analyte on configuration (FIG. 3B), reporter particle 201 is released from first helix strand 211 by chemical analyte 203 and moves away from analysis substrate 205. The reporter particle 201 is attached to nucleic acid core 210 and moves reversibly between the analyte off and analyte on configurations.

In an embodiment, agile nucleic acid sensor array 113 includes a plurality of agile nucleic acid sensors 200, and agile nucleic acid sensor array 113 includes a CMOS chip with integrated circuitry and electrodes (e.g., sensor counter electrode 108, analysis substrate 205, sensor reference electrode 111) that interface to DNA switch 209 via chemical functionalization of the electrodes in an array of agile nucleic acid sensors 200 that measure various biomarkers. FIG. 1 and FIG. 2 show embodiments of CMOS circuitry, or agile nucleic acid sensor array 113 and agile nucleic acid sensor 200 can include other configurations and electronics. The surface functionalization leverages DNA origami nanostructures of DNA switch 209. reporter particle 201 allows a weak signal upon binding of chemical analyte 203 to first helix strand 211 to be amplified. The degree of amplification determines the sensitivity of agile nucleic acid sensor array 113 and can be tuned by the size and charge on the reporter particle 201 to allow measurements of ensembles of chemical analyte 203, e.g., down to a single chemical analyte 203 with a signal to noise ratio (SNR) greater than 20 dB.

The first helix strand 211 allows the strength of the interaction with the chemical analyte 203 to be tuned via sequence mismatches, which alter the thermodynamics of the pair and thereby the kinetics. These engineered weak interactions will allow the chemical analyte 203 to trigger reporter particle 201 to the analyte on position and reversibly return reporter particle 201 to the analyte off position. The measurand is the rate at which the chemical analyte 203 attaches to first helix strand 211 and the rate at which chemical analyte 203 dissociates therefrom. These rate constants can be tuned to vary between milliseconds to minutes and are determined by the strength of the interaction between chemical analyte 203 and first helix strand 211.

The nucleic acid core 210 (e.g., DNA origami) provides a supporting structure to anchor the first helix strand 211 and reporter particle 201. The nucleic acid core 210 can be a six-helix bundle, e.g., as shown in FIG. 3, or another geometric form and can be constructed from DNA or another polymer that selectively attaches chemical analyte 203. The nucleic acid core 210 is a stable structural element for the other components of DNA switch 209 and is an addressable member for disposition of first helix strand 211, e.g., via the sequence of nucleic acid core 210. This allows different versions of nucleic acid core 210 to be altered or paired with different versions of first helix strand 211 in DNA switch 209. In this manner, various agile nucleic acid sensors 200 in agile nucleic acid sensor array 113 independently can have different or identical agile nucleic acid sensors 200. This modularity allows each analysis substrate 205 of the CMOS array to be customized via a different sequence of first helix strand 211. Therefore, each element of agile nucleic acid sensor array 113 can provide a different response to chemical analyte 203 having the same sequence and provide a fingerprint that identifies chemical analyte 203.

Figure 6:
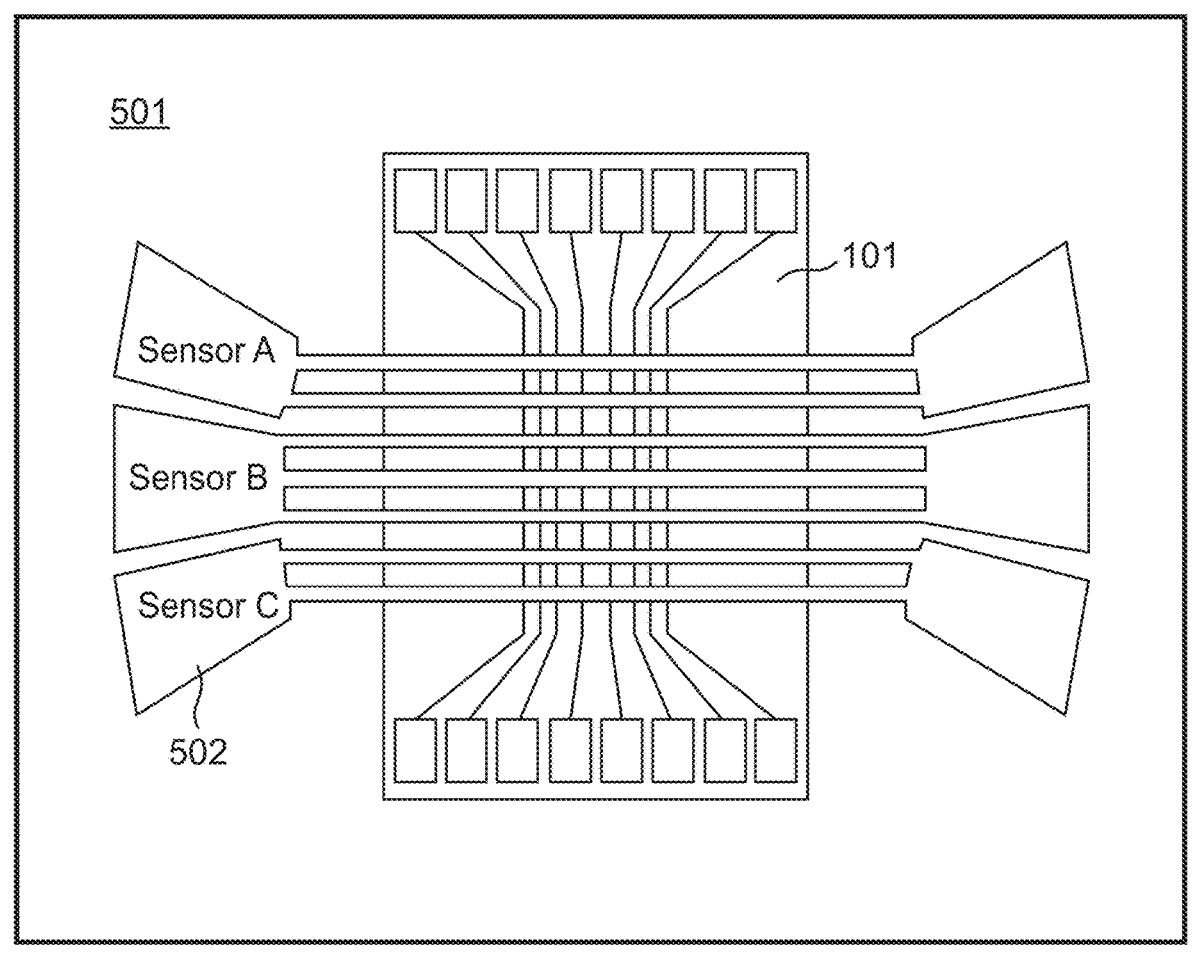
FIG. 6 shows an arrangement for disposing DNA switches on analysis substrates, according to some embodiments.
Figure 7:
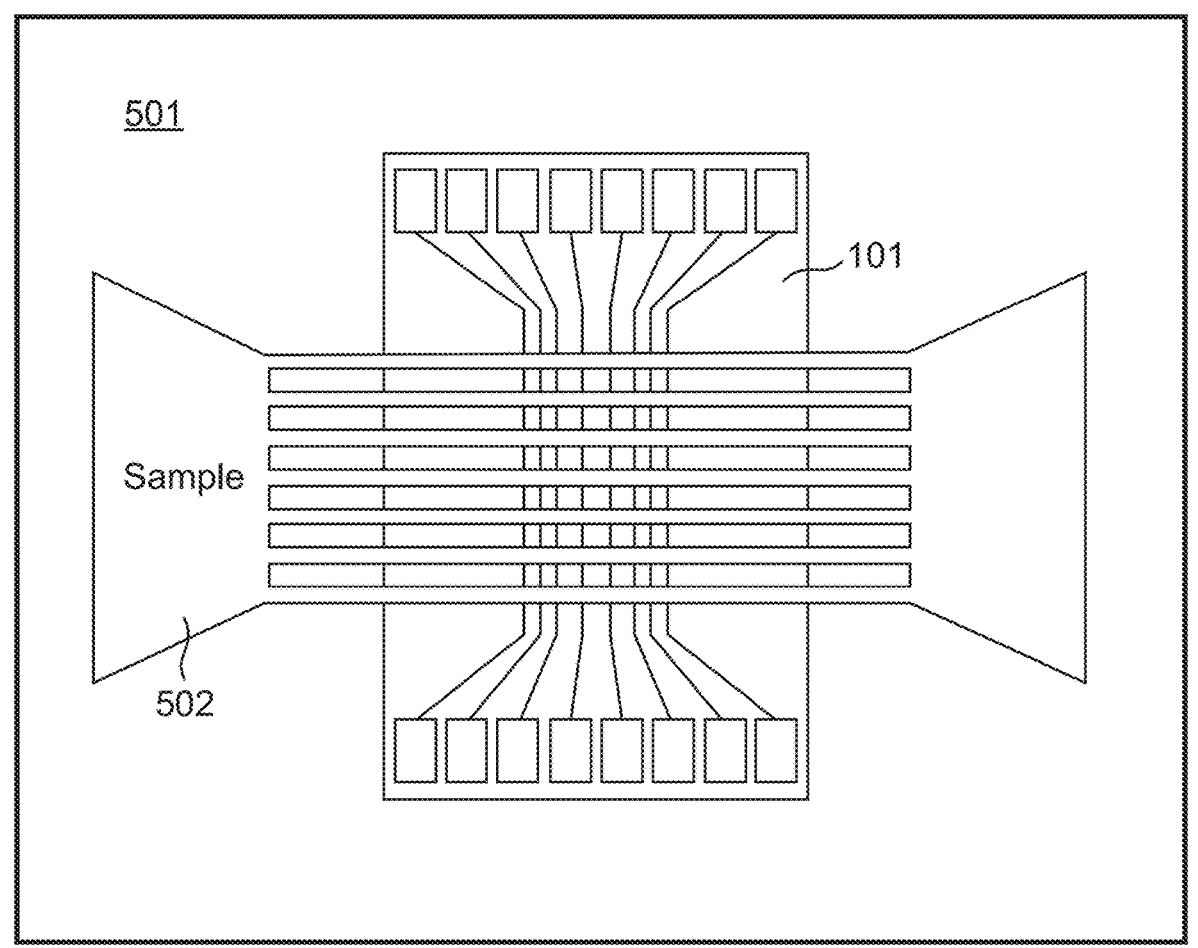
FIG. 7 shows an arrangement for introducing chemical analytes to DNA switches disposed on analysis substrates, according to some embodiments.

With reference to FIG. 6 and FIG. 7, agile nucleic acid sensor array 113 can be made with, operated with, or include fluidics, e.g., microfluidics. Here, microfluidic lines are in fluidic communication with substrate 101. During formation of agile nucleic acid sensor array 113, the microfluidic lines are disposed on substrate 101 such that specific types of agile nucleic acid sensors 200 are formed in selected areas of substrate 101. During operation of agile nucleic acid sensor array 113, the microfluidics lines can be fluidically interconnected to one another such that the individual microfluidics lines are distributed the same composition to every agile nucleic acid sensor 200 in the agile nucleic acid sensor array 113. Similarly, selected microfluidics lines can flow different compositions in an on-demand, manual, or pre-programmed way. The agile nucleic acid sensor array 113 can include fluidic ports on a surface of substrate 101 (e.g., a top, side, or bottom surface) to pump a composition that can include chemical analyte 203 through the microfluid layer that include the microfluidic lines. Electrical connection to elements of the microfluidic lines can be made via pogo pins that are aligned and pressed against electrical pads on substrate 101. During operation, these can be used for sensing. During fabrication, they can be used for electrophoresis to assist in depositing the agile nucleic acid sensors 200. The pogo pins can connect to a circuit board for communicating electrical control signals or acquiring data. The circuit board can be used for deposition during making the agile nucleic acid sensor array 113 or for sensing. Electrical components to operate agile nucleic acid sensor array 113 can be included on the circuit board.

The substrate 101 can be mounted in a package that can form a fluid-tight seal, e.g., by compressing an elastomer such as an O-ring. Compression of the elastomer can occur, e.g., by screws, springs, or the like. Compression of the parts can provide adequate force for electrical contact to the pogo pins.

With reference to FIG. 6, microfluidic package 501 can have fabrication configuration fluid delivery 502, wherein various supply reservoirs (left-hard part in FIG. 6) provide selected compositions to sensors in agile nucleic acid sensor array 113 to form specific agile nucleic acid sensor 200. With reference to FIG. 7, microfluidic package 501 can have sensing configuration fluid delivery 503, wherein a supply reservoir (left-hard part in FIG. 7) provides a composition with chemical analyte 203 to sensors in agile nucleic acid sensor array 113 to form specific agile nucleic acid sensor 200.

The top of microfluidic package 501 can include a top that with fluidic ports used to connect the microfluidic lines, screws holes to compress the microfluidic package 501 and substrate 101, and the like. This provides a fluidic seal and electrical connections. The microfluidic layer of microfluidic lines can be disposed under the top surface of microfluidic package 501 and can be in direct fluidic contact with substrate 101. An O-ring can be interposed between substrate 101 and the microfluidic layer to provide a hermetic seal. The substrate 101 can include through silicon vias to allow components to be disposed on opposing surfaces thereof, e.g., for electrical contact pads to be disposed on the underside of substrate 101 and agile nucleic acid sensor 200 to be disposed on top of substrate 101 to interface with the microfluidics. The bottom of microfluidic package 501 can include pogo pins as electrical conductors and for electrical connections to substrate 101. Pogo pins can be disposed on the underside to interface with a circuit board. The circuit board can include the electrical components needed to operate agile nucleic acid sensor array 113. The microfluidic package 501 can also include members for fasteners, e.g., mounting holes to receive a fastener (e.g., a screw) so that microfluidic package 501 can be mounted (e.g., screwed) to the circuit board.

The microfluidic package 501 can be made in various ways, e.g., 3D printed or machined. The microfluidics layer can be incorporated into the top of microfluidic package 501 as part of the 3D printing or machining process or can be a separate layer that is interposed between substrate 101 and the top. The microfluidics layer can be 3D printed or machined. Alignment pins can be used to align an assemble the components of microfluidic package 501 to substrate 101.

Elements of agile nucleic acid sensor array 113 can be various sizes and can be made of a material that is physically or chemically resilient in an environment in which agile nucleic acid sensor array 113 is disposed. Exemplary materials include a metal, ceramic, thermoplastic, glass, semiconductor, and the like. The elements of agile nucleic acid sensor array 113 can be made of the same or different material and can be monolithic in a single physical body or can be separate members that are physically joined.

Agile nucleic acid sensor 200 and agile nucleic acid sensor array 113 can be made in various ways. It should be appreciated that agile nucleic acid sensor 200 and agile nucleic acid sensor array 113 can include a number of optical, electrical, or mechanical components, wherein such components can be interconnected and placed in communication (e.g., optical communication, electrical communication, mechanical communication, and the like) by physical, chemical, optical, or free-space interconnects. The components can be disposed on mounts that can be disposed on a bulkhead for alignment or physical compartmentalization. As a result, agile nucleic acid sensor 200 and agile nucleic acid sensor array 113 can be disposed in a terrestrial environment or space environment. Elements of agile nucleic acid sensor 200 and agile nucleic acid sensor array 113 can be formed from silicon, silicon nitride, and the like although other suitable materials, such ceramic, glass, or metal can be used, the electrical conductivity of which can be selected according to operation of agile nucleic acid sensor array 113. According to an embodiment, the elements of agile nucleic acid sensor 200 and agile nucleic acid sensor array 113 are formed using 3D printing although the elements of agile nucleic acid sensor 200 and agile nucleic acid sensor array 113 can be formed using other methods, such as injection molding or machining a stock material such as block of material that is subjected to removal of material such as by cutting, laser oblation, and the like. Accordingly, agile nucleic acid sensor 200 and agile nucleic acid sensor array 113 can be made by additive or subtractive manufacturing. In an embodiment, elements of agile nucleic acid sensor 200 are selectively etched to remove various different materials using different etchants and photolithographic masks and procedures. The various layers thus formed can be subjected to joining by bonding to form agile nucleic acid sensor 200 and agile nucleic acid sensor array 113.

The process for making agile nucleic acid sensor 200 also can include forming a DNA nanostructure, e.g., for DNA switch 209, which can include selecting a mechanism for signal amplification (surface charge, capacitance, etc.) and surface binding (gold/thiol, biotin/streptavidin, etc.) of chemical analyte 203 by first helix strand 211 and reporter particle 201; determining a 3D shape of DNA origami of nucleic acid core 210 for sampling on/off binding states associated with signal amplification of contact of DNA switch 209 with chemical analyte 203 as well as positions for surface binding and analyte binding that will lock the shape in the on state; routing viral DNA scaffold through 3D shape; filling in staple strands; truncating to lengths commensurate with desired DNA synthesis technique; and labeling relevant staple positions associated with surface binding and analyte binding for modification with the appropriate chemical moieties.

The process for making agile nucleic acid sensor array 113 also can include forming DNA switch 209 by: combining a viral DNA scaffold, pH buffering components, divalent cations, DNA oligomer staples that fold the body of the nanostructure, and staples that bind the nanostructure to analysis substrate 205, and staples for first helix strand 211, wherein scaffold and staples can be present in a ratio, e.g., from 1:5 to 1:10 or higher; annealing the composition to remove secondary structure, e.g., thermal annealing via heating the composition to 80° C. for denaturing followed by cooling to 25° C. at a cooling rate, e.g., of 1° C./min, or alternatively chemical annealing via dialysis against a formamide gradient; labeling relevant staple positions associated with surface binding and analyte binding for modification with the appropriate chemical moieties; removing excess staples, e.g., via PEG precipitation or molecular weight cutoff spin filter protocols; performing quality control (e.g., gel electrophoresis, microscopy, and the like); and disposing DNA switch 209 on analysis substrate 205 via a protocol that is suitable for the surface binding chemistry being used.

The process for making agile nucleic acid sensor array 113 also can include microfluidically delivering individual DNA switches 209 to individual agile nucleic acid sensors 200 by: forming microfluidic package 501 that holds substrate 101 and microfluidic layers (502 and 503) such that substrate 101 and microfluidic layers can be disassembled and interchanged; configuring the microfluidic package 501 in the first instance for sensor fabrication by disposing the fabrication microfluidic configuration 502 on substrate 101 within microfluidic package 501; delivering different DNA switches 209, aligning and binding DNA switches 209 to predetermined sensor working electrodes 205; functionalizing selected regions of substrate 101 with different sensor types delivered via separate microfluidic lines; and removing substrate 101 from microfluidic package 501 and disposing in a new microfluidic package 501 that contains microfluidics in the sensing configuration 503 for sensor operation.

Agile nucleic acid sensor 200 has numerous advantageous and unexpected benefits and uses. In an embodiment, a process for measuring a biomarker includes: disposing substrate 101 (that includes agile nucleic acid sensor array 113) in microfluidic package 501; providing a microfluidic fabrication fluid delivery layer 502 on substrate 101; delivering differently tuned DNA nanotechnology sensors to individual sensor working electrodes 205 to configure the sensing array for a selected application (e.g., sensing a particular chemical analyte 203); replacing layer 502 with operation fluid delivery microfluidic layer 503; delivering a composition including chemical analyte 203 sample to the sensor array 113; reading out sensing signals using interface pads 112; and analyzing the sensing signals.

Figure 10:
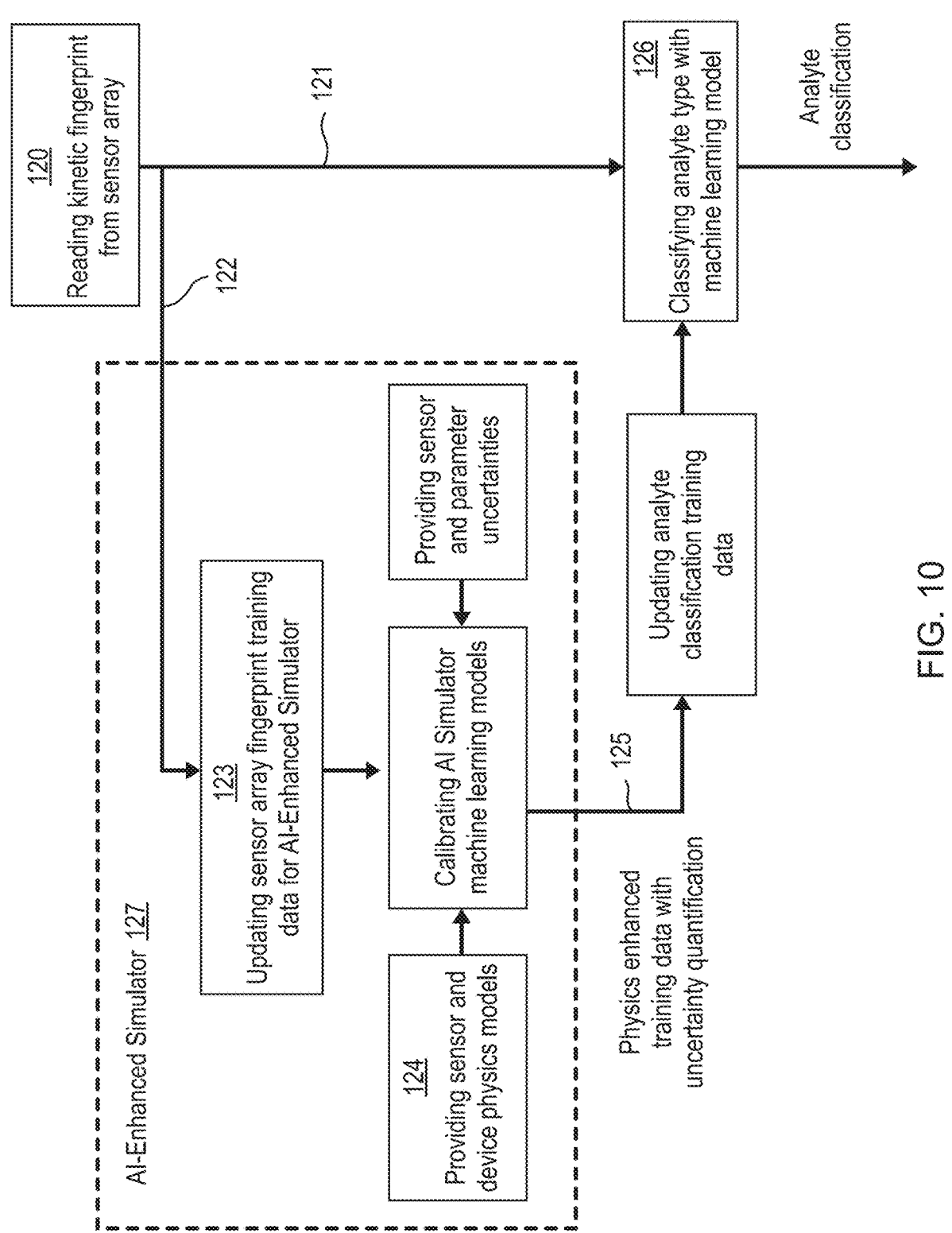
FIG. 10 shows steps in measuring a biomarker with an agile nucleic acid sensor, according to some embodiments.
Figure 11:
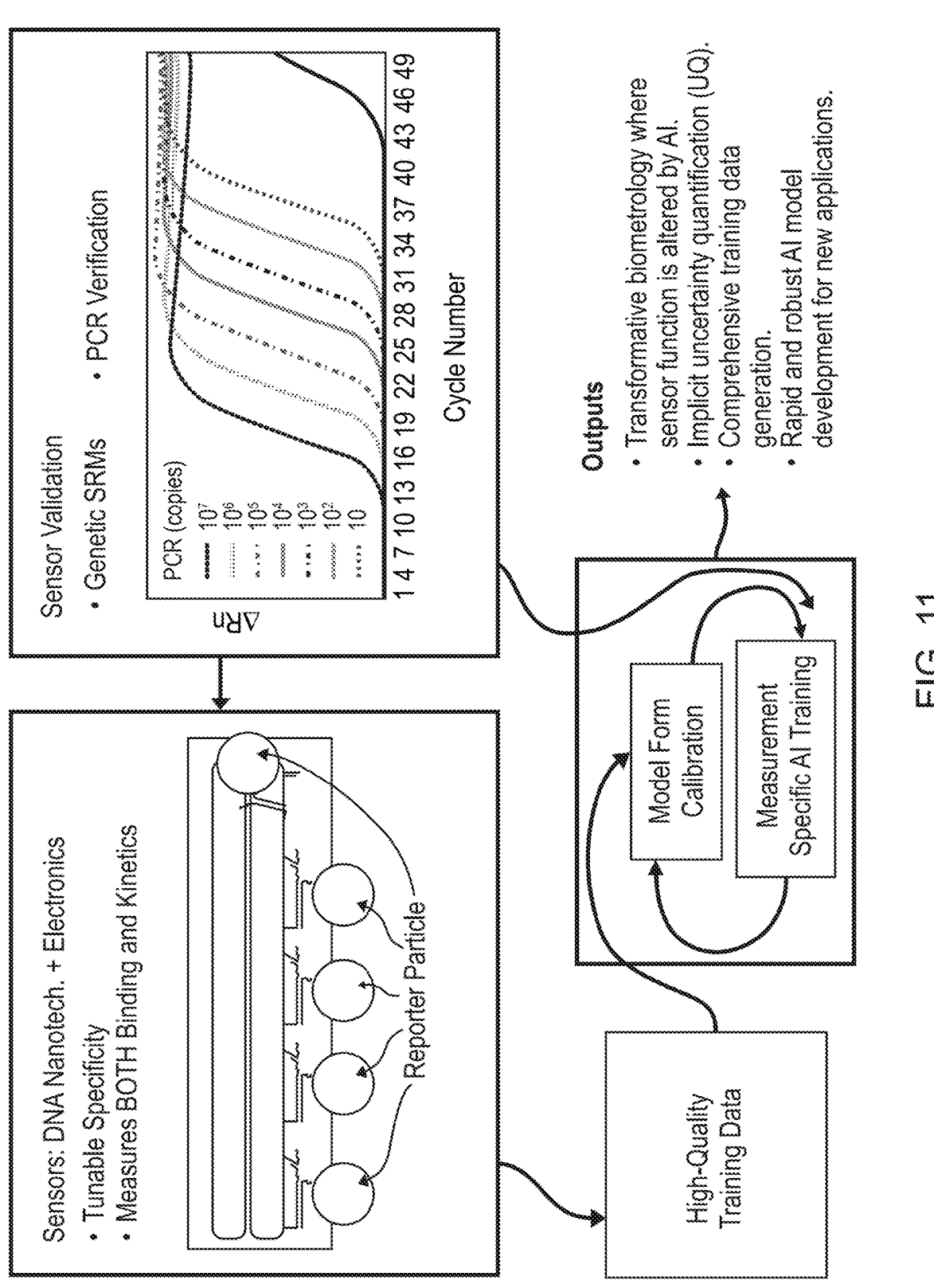
FIG. 11 shows steps in measuring a biomarker with an agile nucleic acid sensor, according to some embodiments.

In an embodiment, with reference to FIG. 9, FIG. 10, and FIG. 11, a process for measuring a biomarker with an agile nucleic acid sensor array 113 includes: operating the agile nucleic acid sensor array 113 that includes: a plurality of agile nucleic acid sensors 200 arranged in array and that individually include: a DNA switch 209; an analysis substrate 205 in electrostatic communication with the DNA switch 209 that is disposed on the analysis substrate 205; a transduction member 114 in electrical communication with the analysis substrate 205; a sensor counter electrode 108 in electrical communication with and capacitively coupled to the analysis substrate 205; a sensor reference electrode 111 in electrical communication and capacitively coupled to the analysis substrate 205; and a voltage follower 109 in electrical communication with the sensor counter electrode 108 and the sensor reference electrode 111; for individual agile nucleic acid sensor 200 in the agile nucleic acid sensor array 113: producing a counter electrode voltage 117 by the voltage follower 109; subjecting the sensor counter electrode 108 to the counter electrode voltage 117 from the voltage follower 109; contacting the DNA switch 209 with a chemical analyte 203 comprising the biomarker; producing, by the analysis substrate 205, a biomarker electrical signal 115 in response to the chemical analyte 203 contacting the DNA switch 209; receiving, by the transduction member 114, the biomarker electrical signal 115 from the analysis substrate 205 and producing a transduction signal 116 from the biomarker electrical signal 115; determining the impedance of the analysis substrate 205 from the transduction signal 116; estimating kinetic rate constants for each contact between the chemical analyte 203 and the DNA switch 209; and combining the kinetic rate constants and producing a mean kinetic rate constant with uncertainty quantification for the kinetic rate constants; aggregating the mean kinetic rate constants for the plurality of agile nucleic acid sensor 200 in the agile nucleic acid sensor array 113; and producing a kinetic fingerprint for the chemical analyte 203 from the mean kinetic rate constants.

With further reference to FIG. 9, FIG. 10, and FIG. 11, the process for measuring a biomarker with agile nucleic acid sensor array 113 can include reading the kinetic fingerprint from the agile nucleic acid sensor array 113 (step 120); providing the kinetic fingerprint as input to a machine learning model for classification (step 121); providing the kinetic fingerprint as input to an AI-enhanced simulator 127 (step 122); updating training data for the AI-enhanced simulator 127 machine learning models (step 123); providing a physical model of the agile nucleic acid sensor 200 and kinetic fingerprint measurement to the AI-enhanced simulator 127 machine learning models (step 124); combining the kinetic fingerprint, physical models, and parameter uncertainties using machine learning model to generate physics enhanced training data with uncertainty quantification (step 125); and combining AI-enhanced simulator training data with the sensor array kinetic fingerprint by analyte classification machine learning to produce analyte classification with uncertatinty quantification (step 126).

The agile nucleic acid sensor array 113 includes dynamic and tunable DNA nanotechnology sensor arrays with 10-fold better LOD (≈10 molecules) than PCR, data-driven modeling, AI classification, UQ, and training data and assay development for detection and classification of chemical analyte 203 of unknown identity.

Figure 18:
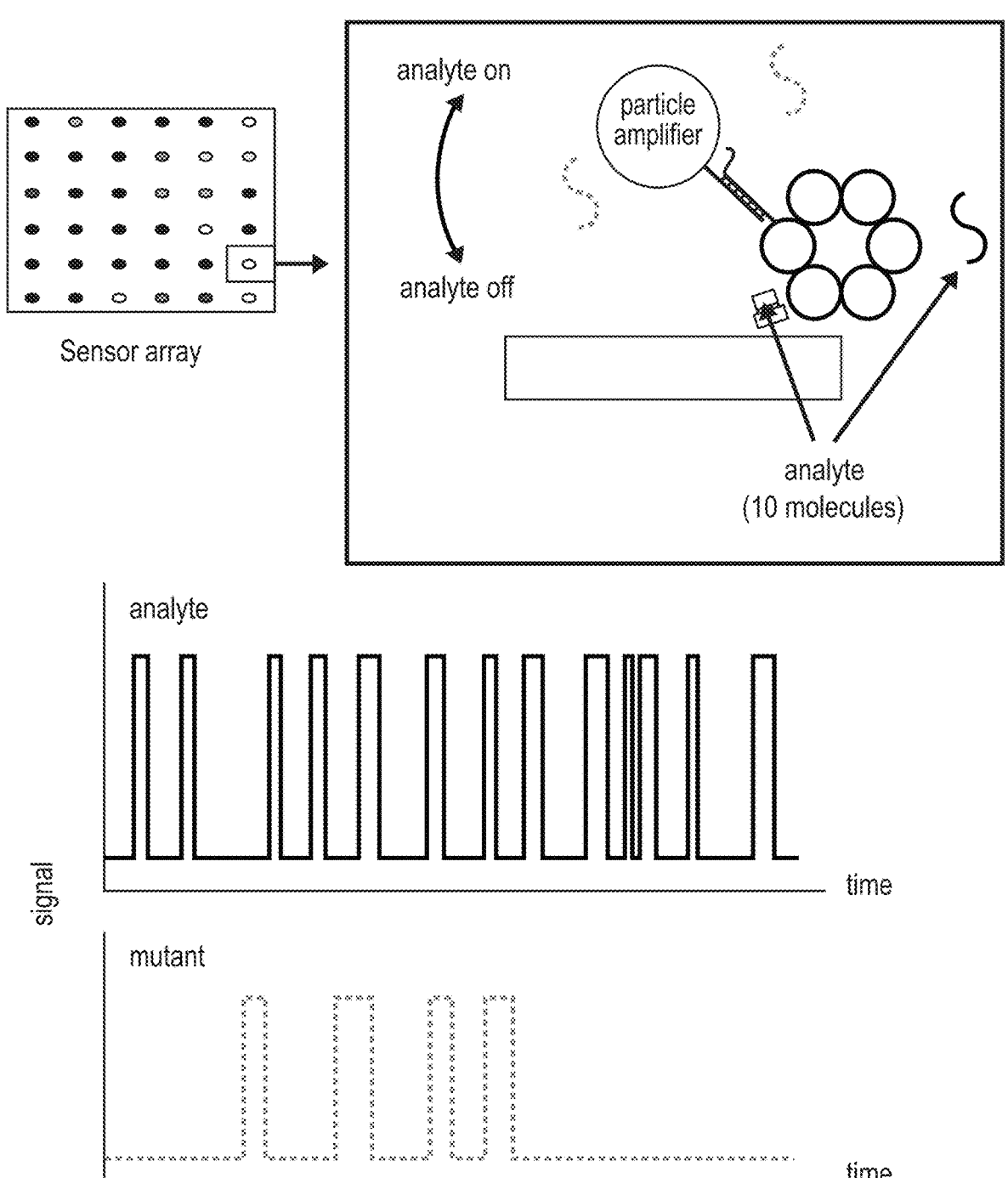
FIG. 18 shows data collection from an agile nucleic acid sensor, according to some embodiments.
Figure 19:
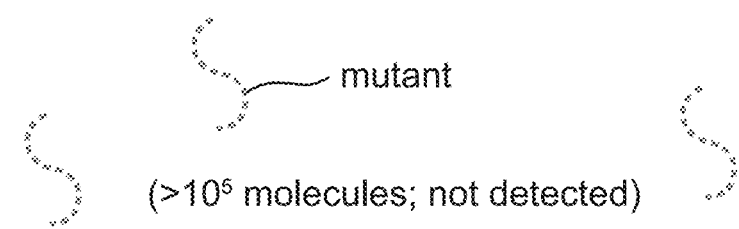
FIG. 19 shows conventional data collection, according to a comparative example.
Figure 19:
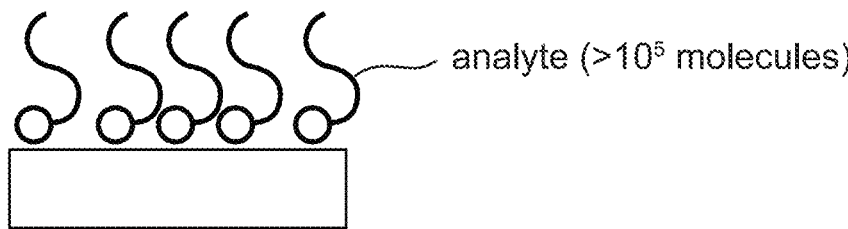
Figure 19:
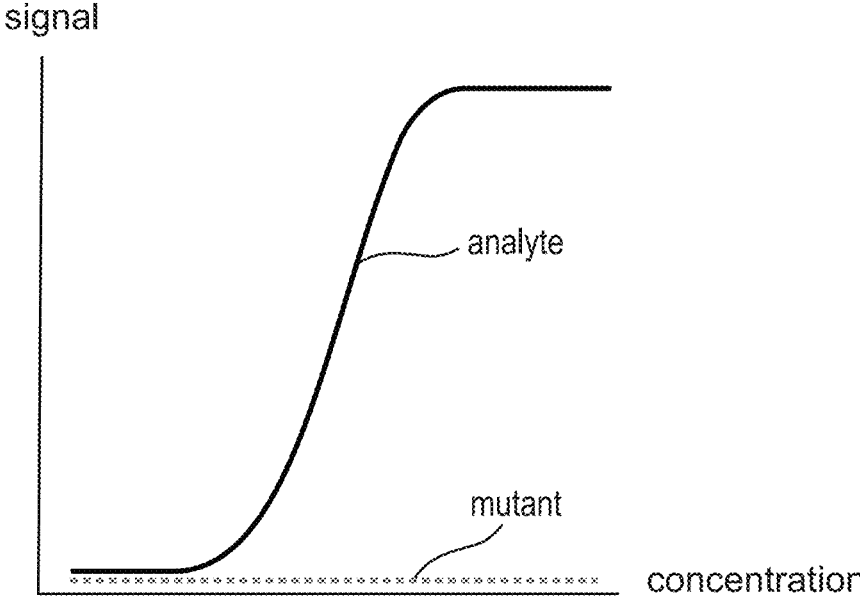

It should be appreciated that agile nucleic acid sensor array 113 is a dynamic and tunable sensor array. Randomly distributed moieties that bind an ensemble of known analytes and produce a signal that monotonically changes with analyte concentration (FIG. 19) underlie conventional bioassays. In contrast, the agile nucleic acid sensor array 113 includes dynamic DNA nanostructures, e.g., agile nucleic acid sensor 200, that allow the strength and duration of the interactions between agile nucleic acid sensors 200 and a target nucleic acid to be precisely defined (FIG. 18). The agile nucleic acid sensor array 113 produces a series of weak interactions between chemical analyte 203 and multiple agile nucleic acid sensors 200 in agile nucleic acid sensor array 113. The sum of which results in a unique molecular signature. Changes in the nucleic acid sequence (e.g., from mutant strains) modify the interactions between the chemical analyte 203 and agile nucleic acid sensors 200, altering the binding with individual agile nucleic acid sensors 200 and changing the molecule signature.

The agile nucleic acid sensor array 113 includes agile nucleic acid sensor 200 with a level of detection (LOD) of ≈10 molecules, ≈$10^4$ molecules, or better than conventional measurements, e.g., electrochemical detection, fluorescence, and the like. This LOD is achieved by designing DNA nanostructures 209 with in-situ reporter particles 201 that enhance the electrostatic potential output by the agile nucleic acid sensor 200 (FIG. 18) and leverages the strand displacement technique to reversibly distinguish the bound and unbound states of chemical analyte 203 chemical analyte 203. The result is engineered detectors (FIG. 18) with precise interaction kinetics defined by the DNA sequence and with tunable gain (e.g., greater than $10^4$) via particle size to allow label-free and PCR-free measurements.

The agile nucleic acid sensors 200 ordered in agile nucleic acid sensor array 113 are configured for highly multiplexed measurements and to minimize variation in detection of chemical analyte 203 among agile nucleic acid sensors 200. For precise fabrication, alignment of agile nucleic acid sensor 200 during fabrication can be achieved by different methods. Electrophoresis can be used, wherein the DNA based sensors 200 are aligned to an applied electric field. The electrodes for alignment can be incorporated in the substrate 101 or can be external. Alternatively, flow in microfluidic channels can be used, wherein the flow can align the sensors 200. Flexibility can be built into by including swappable microfluidic layers, wherein one design for the microfluidic layers is used during fabrication and then replaced with a separate design that is optimized for operation of the sensor.

Advantageously, agile nucleic acid sensor array 113 includes a high resolution electronic readout of sensor 200 with field-effect transistors (FETs) for measurement of dynamic quantities shown in FIG. 18. These can include (a) the sensor type and sequence from the signal amplitude, (b) the association rate to allow estimation of analyte concentration, and (c) the interaction strength from the dissociation rate. These multi-variate measurands, combined across all sensors 200, provide the AI-enhanced simulator 127 data that is labelled for classification.

Optimization of the sensors 200 provide mitigation of entropic penalty of reporter particle 201 that can hinder multiplexing, by:

optimizing binding kinetics through control of the DNA nanostructure 202 sequence;

including of cycles of PCR to improve the signal-to-noise-ratio (SNR);

varying the counterion concentration to control electrostatic interactions between the DNA strands;

altering sensor temperature to provide energetic control of the kinetic interaction;

metering probe-target concentrations to vary sensitivity;

delivering, by microfabrication and microfluidics, different DNA structures, each with predetermined tunability, to separate regions of substrate 101;

using microfabrication to dispose individual sensor elements to minimize crosstalk between measurement channels; or using modified DNA/RNA bases to modify inter-strand interactions.

Data acquired, e.g., by, can be subjected to AI modeling to determine uncertainty. The DNA sensor array 113 can interact with an AI framework for robust data reduction. Conventional analyses iteratively solve a physical model while varying the input parameters to approximate a measured signal, but this can be computationally expensive and can involve the solution of partial-differential equations (PDEs) that describe an exponential number of reaction-diffusion processes due to competing binding interactions. Moreover, relying on purely mathematical models that do not capture the underlying physics can produce overfitting and high uncertainties.

With agile nucleic acid sensor array 113, the data-driven and hierarchal process for measuring a biomarker includes AI elements that reduce order modeling and involve forward solutions of a physical model, based on design of a measurement to train a deep neural network (DNN) that characterizes the relationship between model inputs, e.g., binding affinities and competitive effects, and outputs, e.g., FET voltages.

Subsequently, experimental training data is used to optimize the AI models and identify the dominant competitive effects to determine the classifier for a given analyte. To verify model assumptions, algorithms are tested on a suite of synthetic data and later with measured data. Because the DNN approximates model solutions for a continuum of conditions that occupy a high-dimensional space, the process selects the most promising approach after testing discretization schemes with experimental data. Developing the model forms and training data improves transformation and representation of the measurands and UQ.

With regard to training Data and multiplexed measurements by, training data is used for AI classification of signals from the sensor array 113. Here, AI improves the physical description of sensors 200 and uses this improved reduced order description to train a classifier such as a DNN. A series of experiments under varying sensor parameters is used to generate data to train the reduced order AI models. DNA nanostructures 209, informed by the AI, are then be designed to detect standard reference materials (SRMs) with >95% confidence in the presence of confounding molecules from a viral multiplex reference panel, e.g., as described in Viral Multiplex Reference 11/242, available from the National Institute for Biological Standards and Control at https://www.nibsc.org/products/brm_product_catalogue/detail_page.aspx?catid=11/242 (as of 2022). Final AI training data is generated by systematically sampling system parameters (FIG. 18) within limits determined by the model. This, in turn, allows the PCR-free detection of challenge samples, e.g., including novel SARS-CoV-2 variants in presence of background molecules without prior training of the AI.

The articles and processes herein are illustrated further by the following Examples, which are non-limiting.

EXAMPLE 1

Figure 16:
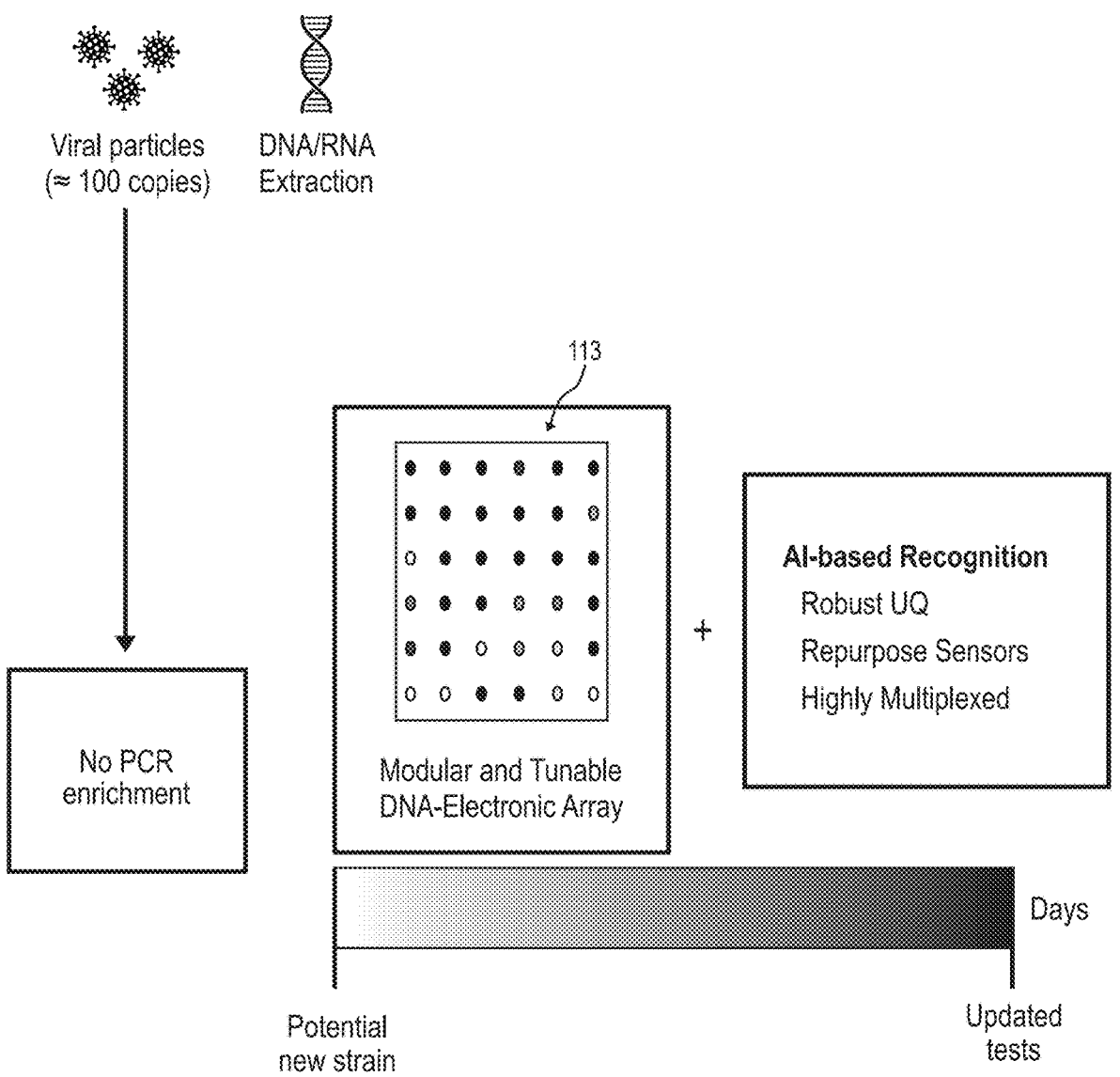
FIG. 16 shows a measurement outline for measuring a biomarker, according to some embodiments.

The agile nucleic acid sensor array 113 upends conventional wisdom of requiring perfect sequence complementarity for robust detection. With reference FIG. 16, agile nucleic acid sensor array 113 includes agile nucleic acid sensors 200 that include DNA switch 209 that are interrogated electronically and measure with a sufficient LOD to eliminate need for PCR enrichment. Instead of designing sensors optimized for a known target, agile nucleic acid sensors 200 in agile nucleic acid sensor array 113 can be heterogenous detectors whose interactions with chemical analyte 203 produce a series of weak interactions. The composite of these interactions produce complex, high-dimensional signals that are ideal for processing with a properly trained AI framework, for highly multiplexed measurements. The sensor array can be tuned for different purposes and circumstances in the field by importing different training of the AI.

The AI here excels at extracting information from signals arising from a complex combination of competing physical processes, some of which obscure the measurand. When the dominant physical processes and their interplay are difficult to describe a priori, AI techniques succumb to either model errors or overfitting, which increase uncertainty. This data-driven approach addresses this problem by first inverting the typical role of AI to identify physical processes that dominate a measurement. This facilitates AI tools to accurately classify the data output by the sensors with a quantitative measure of the associated uncertainties.

COMPARATIVE EXAMPLE 1

Figure 17:
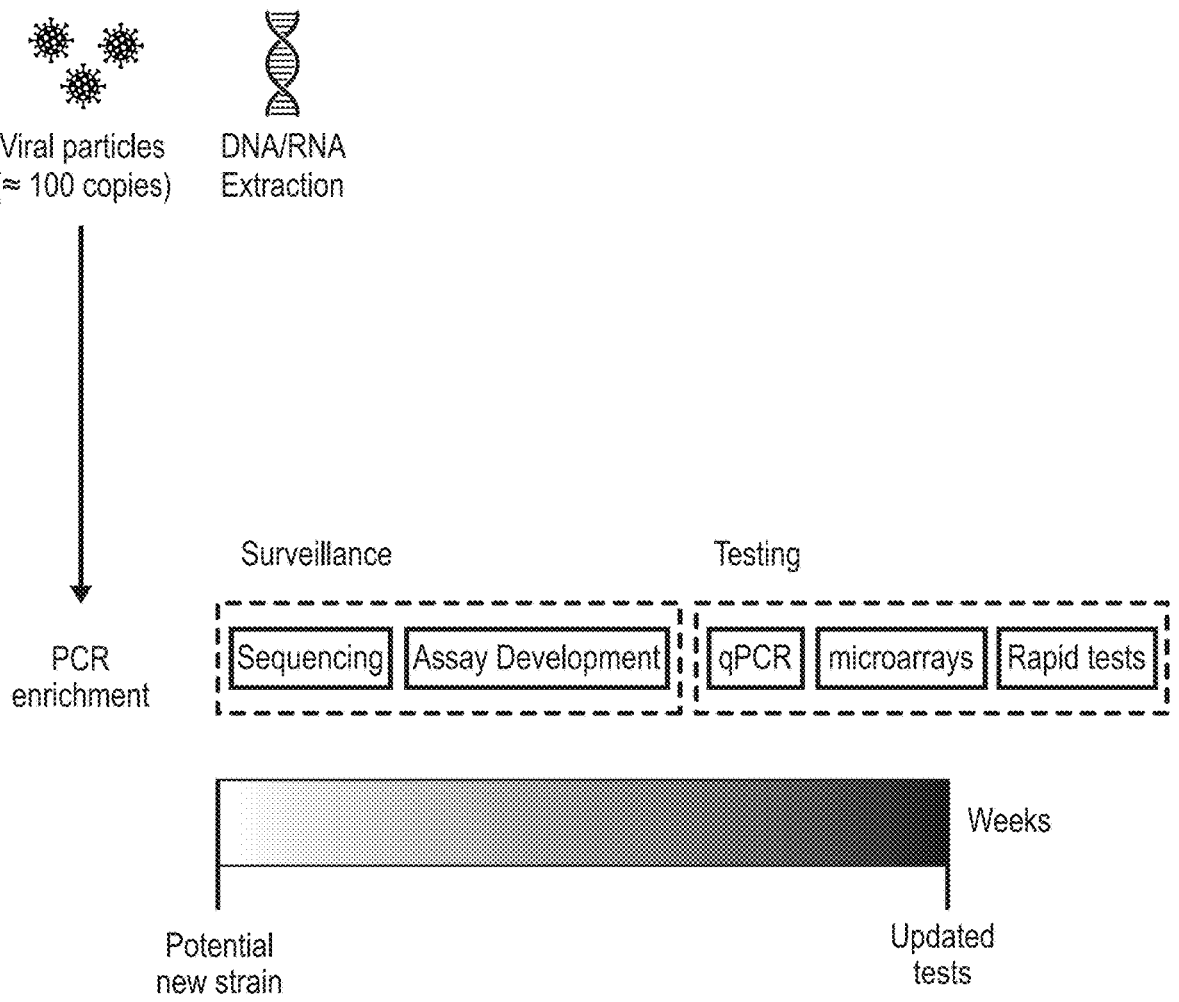
FIG. 17 shows a conventional measurement outline, according to a comparative example.

With reference to FIG. 17, conventional nucleic acid diagnostic measurements rely on sequence complementarity (the canonical pairing of G to C or A to T over a region of DNA). This property has been the foundation of medical testing for decades. It underlies quantitative PCR (qPCR), the conventional method in viral detection that can distinguish analytes with subtle differences, e.g., to separate distinct strains of seasonal influenza from the SARS coronavirus, with a limit-of-detection (LOD) of 100 molecules. However, PCR techniques are hindered by low multiplexing (e.g., qPCR is limited to the simultaneous detection of up to five regions of the genome in a single test). Sequence complementarity is also central to DNA microarrays, used to screen for mutations that underlie cancer sub-types, which allow multiplexed detection of hundreds of thousands of known sequences, albeit with LOD>$10^5$ molecules. Similarly, other sequencing schemes allow highly multiplexed measurements but require large amounts of sample and a complex analysis pipeline. In these conventional cases, a specific target region of interest must be known a priori, and the assays optimized to achieve reliable detection. Moreover, sequence mismatches due to assay design errors cause inadequate PCR amplification or incomplete binding in DNA microarrays, resulting in test failures or inconclusive results. The strong dependence of assay performance on sequence complementarity hinders the application of conventional tests to evolution scenarios (e.g., genetic mutations arising from cancer sub-types or rapidly mutating viruses) such that new assays have to be developed for each variant.

EXAMPLE 2

FIG. 8 shows an exemplary design and fabrication of a nucleic acid origami structure for DNA switch 209. The notched rectangle origami design process (FIG. 8, middle panel) shows the M13 scaffold DNA and the location of the staple strands that bind the scaffold to allow the final shape. The structure was verified using AFM imaging (FIG. 8, top panel). The structures are held by thiol bonds to a gold surface (blue dots) and designed to actuate by 6.6 nm away from the surface upon binding of an analyte to the lock strand (red dot). The movement of the highly charged origami away from the surface provides charge amplification similar to a gold nanoparticle covered with DNA or other charged entities.

The kinetics of the switching behavior are controlled by the sequence of the lock motif and can be tuned by introducing different lock strand sequences. A key idea is that the lock strand is highly customizable and modular since the DNA origami scaffold provides an addressable way of customizing this first helix strand 211 sequence without altering the functionality of the rest of the structure. Therefore this approach can be used to generate a multitude of DNA-origami structures that provide a different response to one or more chemical analytes 203.

Figure 12:
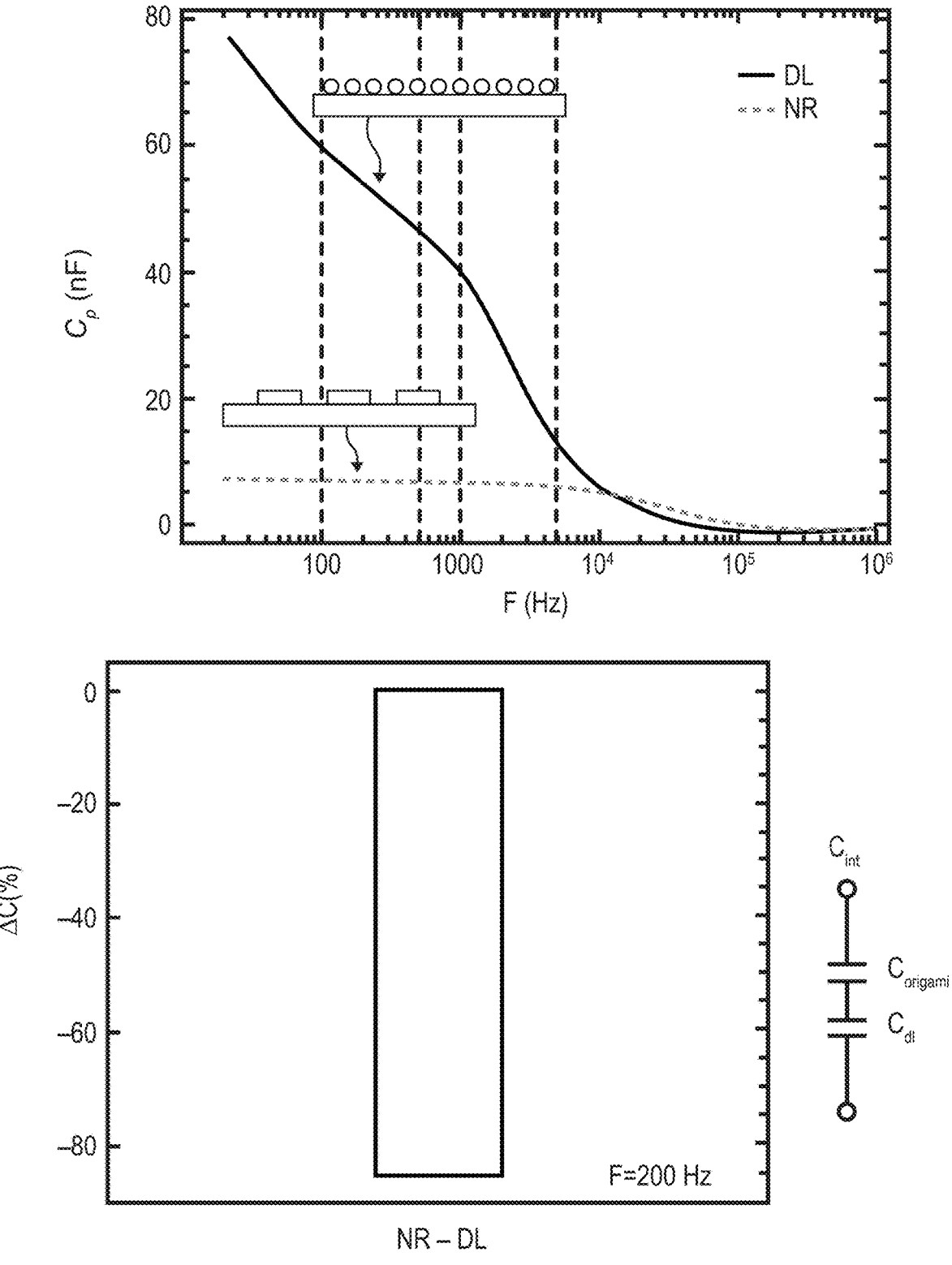
FIG. 12 shows several graphs for quantifying surface functionalization of sensor working electrode with notched rectangle origami, according to some embodiments.

The functionalization of the working electrode 205 was quantified using electrical measurements of the surface capacitance shown in FIG. 12. The capacitance measurements were performed in electrolyte solution as a function of the excitation frequency of an applied sinusoidal AC voltage.

For the bare electrode surface, a high double layer capacitance was measured. Upon adding the notched rectangle origami this capacitance dropped drastically (>80% at 100 Hz) indicating a significant increase in the thickness of species adsorbed to the surface. The addition of the origami to the surface resulted in an effective circuit model that had two capacitors in series as shown in FIG. 2 (bottom right), and the density of notched rectangle origami on the surface was $1.2 \times 10^9$ cm$^{-2}$ or covering approximately 7% of the sensor surface.

Figure 13:
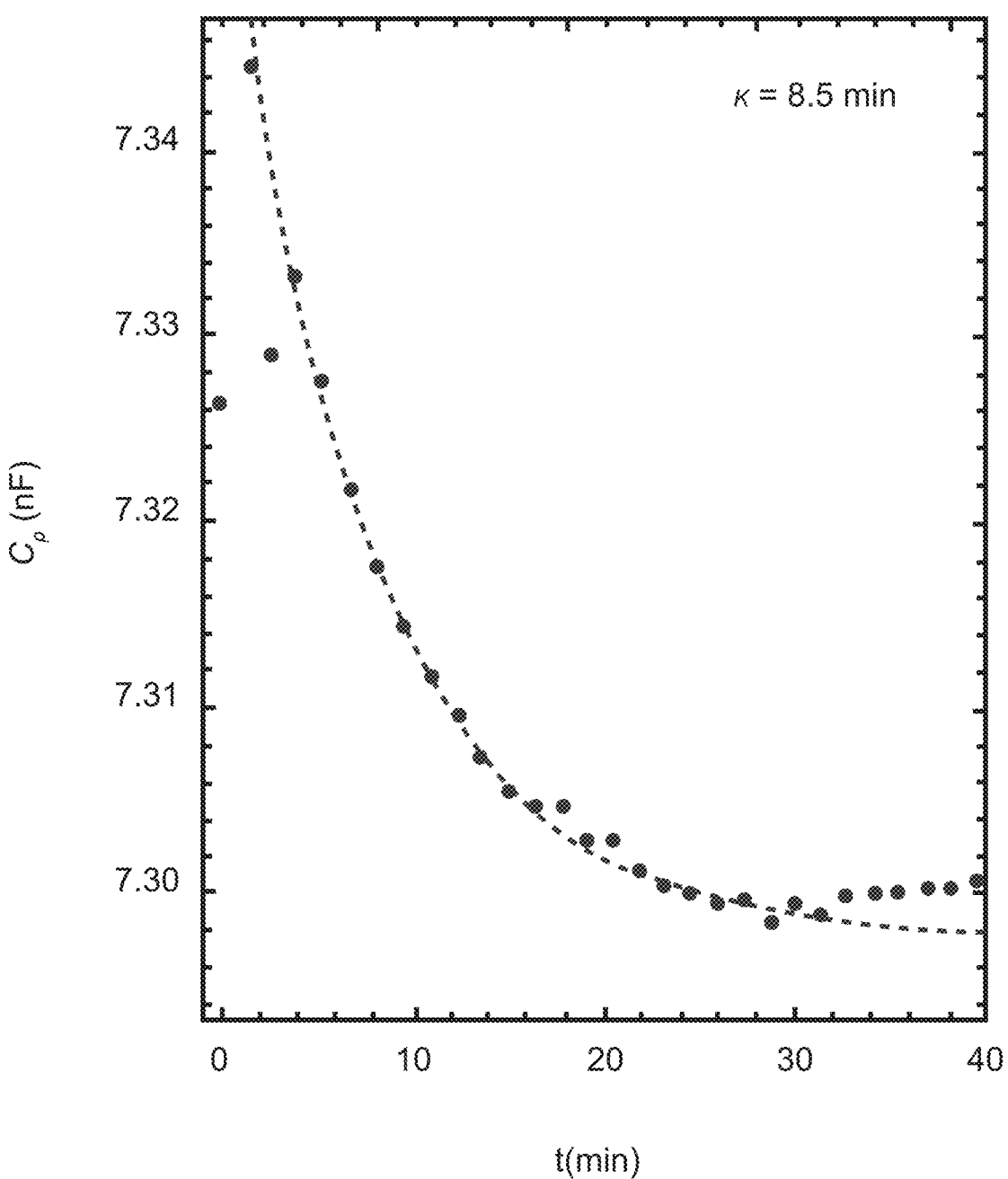
FIG. 13 shows a kinetic response of notched rectangle origami to analyte, according to some embodiments.

The actuation of the notched rectangle origami was confirmed by adding an analyte that had a complementary sequence to the lock strand of first helix strand 211 (FIG. 8). The actuation was verified by measuring the change in the capacitance as a function of time at the surface of the working electrode at 100 Hz as shown in FIG. 13. The plot shows the aggregate response of all structures on the surface. Assuming a first order response, the kinetic association time was determined to be ~8 minutes.

Figure 14:
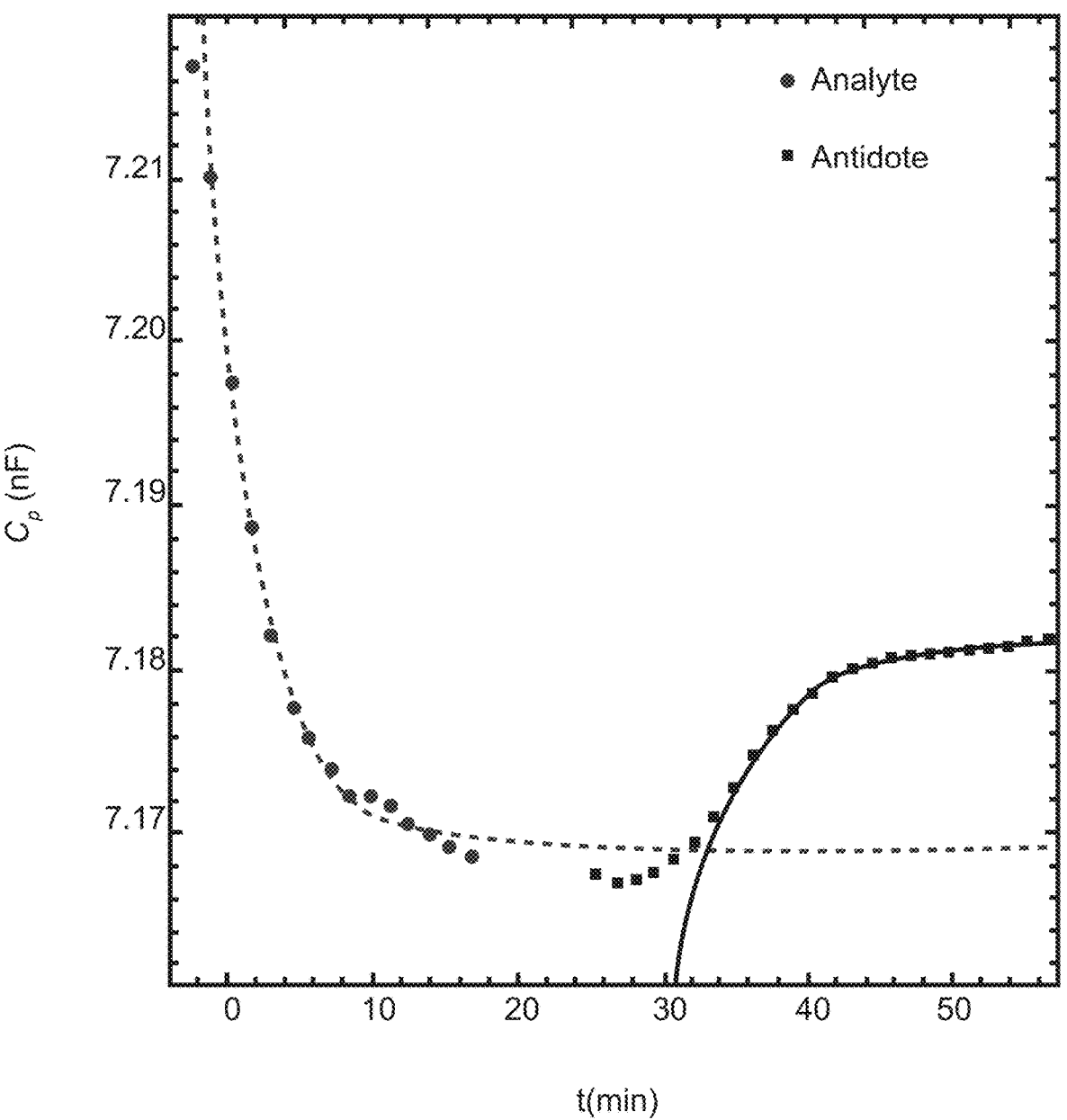
FIG. 14 shows a kinetic recovery of notched rectangle origami demonstrating reversibility, according to some embodiments.

The reprogrammability of the method was verified by competitively dissociating the analyte from the lock strand using the strand displacement technique. An antidote strand that had a high affinity for the analyte was used to dissociate the strand and return the structure to its analyte off position on the surface of the electrode as shown in FIG. 14. The ability to measure the kinetic association and dissociation of an origami structure provides the basis for reprogrammability of the sensor array and will enable scaling for highly multiplexed measurements.

EXAMPLE 3

Multiplexed biomarker measurements distinguish analytes with subtle but important differences, e.g., separating distinct strains of seasonal influenza from the SARS coronavirus. The measurements can detect several types of genetic mutations that underly cancers. In all cases, the development of a new assay is slow, expensive and error-prone.

The are PCR-free measurements of RNA or DNA at extremely low copy numbers, with data analysis performed with AI. The sensors 200 include electronic detectors, and each includes DNA switch 209 whose sequence complementarity for an analyte determines the energetics of the interaction. This energy barrier controls both the analyte binding affinity via the thermodynamics and the interaction kinetics. Because many detectors populate a given sensor, competitive interactions between them lead to complex, high-dimensional signals that are ideal for processing with an AI framework. The AI implements a rich mathematical structure that allows the flexible sensors to be recalibrated on-the-fly (via reference data) to detect new analytes, e.g., those associated with emerging diseases. Moreover, this approach can be adapted to existing measurements, such as DNA microarrays resulting in even broader impact.

The AI here provides reduced-order modeling. AI excels at extracting information from signals arising from a complex combination of competing physical processes, some of which obscure the measurand. This ability is predicated on having a model that is sufficiently rich to accurately describe these underlying processes. However, when the dominant physical processes and their interplay are difficult to describe efficiently a priori, AI techniques succumb to either model errors or overfitting, both of which increase uncertainty. The uses a data-driven process that overcomes this problem by inverting the role of AI, by using it to first identify physical processes that dominate a measurement. This allows for efficient characterization of the measurement processes and for downstream AI tools to accurately characterize the measurements.

With regard to uncertainty, incorporation of uncertainty quantification (UQ) within an AI framework is challenging. Here, the AI includes forward and inverse modeling of the high-dimensional, multi-scale, and multi-physics parameter space associated with our measurements. The analysis yield a quantitative understanding of uncertainties and inadequacies in mathematical models, resulting in a new stochastic design paradigm for biomarker measurements.

Training data is used. Adding an additional composite layer of optimization to allow UQ increases reliance of AI models on the quality and quantity of training data. The agile nucleic acid sensors 200 can generate large and comprehensive reference measurements tailored for AI. A defined sequence mismatch between the DNA nanostructures 209 and measured nucleic acid analytes 203 allows affinity and kinetics of the interactions to be varied systematically to generate unique high-dimensional training data.

Sensors 200 that combine DNA nanotechnology with sensitive electronics are validated with genetic SRMs measured using quantitative PCR (qPCR) and digital PCR (dPCR) measurements. The feedback loop resulting from using the DNA nanodevices 200 to generate the large amount of high-quality training data needed to develop the AI models, which in turn results in robust biometrology (FIG. 11).

Data analyses can iteratively solve a model of a physical system while varying input parameters to match the output with an acquired signal and deduce optimal information about a measurand. This approach can be computationally expensive for use with physical models of our sensor array, which includes partial-differential equations (PDEs) that describe many reaction-diffusion processes combinatorially due to competitive binding interactions. Relying solely on mathematical models that do not capture the underlying physics can result in overfitting and high uncertainties. Therefore, and measuring a biomarker involves a hierarchal framework that leverages AI for reduced order modeling and includes forward solutions of a physically-informed model once upon design of a measurement. A deep neural network (DNN) is trained to characterize the relationship between model inputs, e.g., binding affinities and competitive effects, and outputs, e.g., voltages on sensor working electrode 205.

Empirical data was used to optimize the AI model and identify dominant competitive effects to determine the classifier for a given chemical analyte 203. Making this classification scheme includes selection of basis functions that: approximate the underlying physical processes through the construction of a loss function, reduce dimensional complexity of the model, allow efficient training and information extraction, and estimate errors associated with ignoring non-dominant effects.

To verify model assumptions, the algorithms are tested on a suite of synthetic data and later with measured data. Because the DNN approximates solutions to our model for a continuum of conditions that occupy a high-dimensional space, our approach allows us to select the most promising approach after testing a myriad discretization schemes with the measured data. This step can be performed iteratively with the sensor development for optimal measurements.

Figure 15:
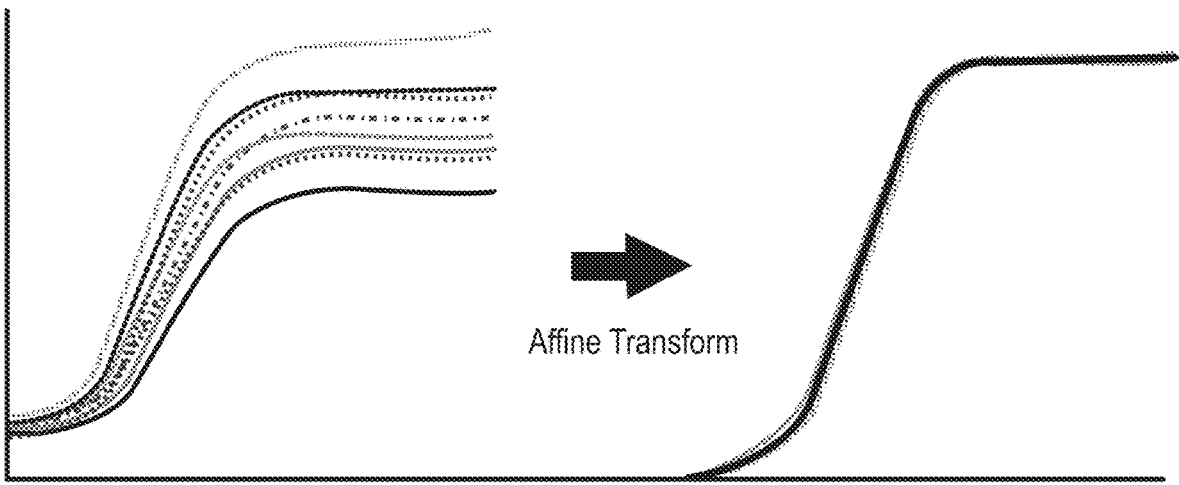
FIG. 15 shows qPCR data correction with an affine transform, according to some embodiments.

Developing the appropriate model forms and training data allow improved transformation and representation of the measurands and robust UQ. Data for this are shown in FIG. 15 that uses affine transforms to accurately estimate qPCR uncertainty.

The following are incorporated by reference herein in their entirety:

GIS Aid. SARS-CoV2 Variants available at https://www.gisaid.org/hcov19-variants/.

Revealing thermodynamics of DNA origami folding via affine transformations. Nucleic Acids Res. gkaa283 (2020) doi:10.1093/nar/gkaa283.

Dynamic DNA nanotechnology using strand-displacement reactions. Nat. Chem. 3, 103-113 (2011).

An easy-to-prepare mini-scaffold for DNA origami. Nanoscale 7, 16621-16624 (2015).

Reproducible Performance Improvements to Monolayer MoS2 Transistors through Exposed Material Forming Gas Annealing. ACS Appl. Mater. Interfaces 11, 16683-16692 (2019).

Rapid, quantitative therapeutic screening for Alzheimer's enzymes enabled by optimal signal transduction with transistors. The Analyst 145, 2925-2936 (2020).

Quantum capacitance-limited MoS2 biosensors enable remote label-free enzyme measurements. Nanoscale 11, 15622-15632 (2019).

Charge detector and process for sensing a charged analyte. US Patent Application Publication No. 2020/0264129.

Structure and Process For High-Resolution Biosensor Charge Readout With Silicon Transistors. U.S. patent application Ser. No. 17/029,999.

Scalable nano-bioprobes with sub-cellular resolution for cell detection. Biosens. Bioelectron. 45, 267-273 (2013).

Diffusion-limited reactions in nanoscale electronics. Methods Appl. Anal. 26, 149-166 (2019).

Mass spectral similarity mapping applied to fentanyl analogs. Forensic Chem. 100237 (2020) doi:10.1016/j.forc.2020.100237.

Stochastic regression modeling of chemical spectra. Chemom. Intell. Lab. Syst. 139, 26-32 (2014).

Affine analysis for quantitative PCR measurements. Anal. Bioanal. Chem. 412, 7977-7988 (2020).

Viral Multiplex Reference, available at https://www.nibsc.org/products/brm_product_catalogue/detail_page.aspx? catid=11/242.

Grand View Research. Infectious Disease In-vitro Diagnostics Market Size, Share & Trends Analysis Report By Product, By Application, By Technology (Immunoassay, Molecular Diagnostics), By End-use, By Region, And Segment Forecasts, 2021-2028, available at https://www.grandviewresearch.com/industry-analysis/ivd-infectious-disease-market.

A Letter to Dr. Eric S. Lander, the President's Science Advisor and nominee as Director of the Office of Science and Technology Policy, available at https://www.whitehouse.gov/briefing-room/statements-releases/2021/01/20/a-letter-to-dr-eric-s-lander-the-presidents-science-advisor-and-nominee-as-director-of-the-office-of-science-and-technology-policy/.

The market trend analysis and prospects of cancer molecular diagnostics kits. Biomater. Res. 22, 2 (2018).

The processes described herein may be embodied in, and fully automated via, software code modules executed by a computing system that includes one or more general purpose computers or processors. The code modules may be stored in any type of non-transitory computer-readable medium or other computer storage device. Some or all the methods may alternatively be embodied in specialized computer hardware. In addition, the components referred to herein may be implemented in hardware, software, firmware, or a combination thereof.

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

Any logical blocks, modules, and algorithm elements described or used in connection with the embodiments disclosed herein can be implemented as electronic hardware, computer software, or combinations of both. To clearly illustrate this interchangeability of hardware and software, various illustrative components, blocks, modules, and elements have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described or used in connection with the embodiments disclosed herein can be implemented or performed by a machine, such as a processing unit or processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein.

A processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile.

While one or more embodiments have been shown and described, modifications and substitutions may be made thereto without departing from the spirit and scope of the invention. Accordingly, it is to be understood that the present invention has been described by way of illustrations and not limitation. Embodiments herein can be used independently or can be combined.

All ranges disclosed herein are inclusive of the endpoints, and the endpoints are independently combinable with each other. The ranges are continuous and thus contain every value and subset thereof in the range. Unless otherwise stated or contextually inapplicable, all percentages, when expressing a quantity, are weight percentages. The suffix (s) as used herein is intended to include both the singular and the plural of the term that it modifies, thereby including at least one of that term (e.g., the colorant(s) includes at least one colorants). Option, optional, or optionally means that the subsequently described event or circumstance can or cannot occur, and that the description includes instances where the event occurs and instances where it does not. As used herein, combination is inclusive of blends, mixtures, alloys, reaction products, collection of elements, and the like.

As used herein, a combination thereof refers to a combination comprising at least one of the named constituents, components, compounds, or elements, optionally together with one or more of the same class of constituents, components, compounds, or elements.

All references are incorporated herein by reference.

The use of the terms "a," "an," and "the" and similar referents in the context of describing the invention (especially in the context of the following claims) are to be construed to cover both the singular and the plural, unless otherwise indicated herein or clearly contradicted by context. It can further be noted that the terms first, second, primary, secondary, and the like herein do not denote any order, quantity, or importance, but rather are used to distinguish one element from another. It will also be understood that, although the terms first, second, etc. are, in some instances, used herein to describe various elements, these elements should not be limited by these terms. For example, a first current could be termed a second current, and, similarly, a second current could be termed a first current, without departing from the scope of the various described embodiments. The first current and the second current are both currents, but they are not the same condition unless explicitly stated as such.

The modifier about used in connection with a quantity is inclusive of the stated value and has the meaning dictated by the context (e.g., it includes the degree of error associated with measurement of the particular quantity). The conjunction or is used to link objects of a list or alternatives and is not disjunctive; rather the elements can be used separately or can be combined together under appropriate circumstances.

What is claimed is:

1. A process for measuring a biomarker with an agile nucleic acid sensor array, the process comprising:

operating the agile nucleic acid sensor array that comprises:

a plurality of agile nucleic acid sensors arranged in array and that individually comprise:

a DNA switch comprising a DNA nanostructure framework disposed on an analysis substrate and comprising a nucleic acid core, a first helix strand protruding from the nucleic acid core and attached to the analysis substrate, a second helix strand protruding from the nucleic acid core, a particle strand hybridized to the second helix strand, and a reporter particle attached to the particle strand;

the analysis substrate in electrostatic communication with the DNA switch that is disposed on the analysis substrate, wherein the second helix strand is hybridized to the first helix strand in an absence of a chemical analyte such that the reporter particle is disposed proximate to the analysis substrate;

a transduction member in electrical communication with the analysis substrate;

a sensor counter electrode in electrical communication with and capacitively coupled to the analysis substrate;

a sensor reference electrode in electrical communication and capacitively coupled to the analysis substrate; and a voltage follower in electrical communication with the sensor counter electrode and the sensor reference electrode;

for individual agile nucleic acid sensor in the agile nucleic acid sensor array:

producing a counter electrode voltage by the voltage follower;

subjecting the sensor counter electrode to the counter electrode voltage from the voltage follower;

contacting the DNA switch with the chemical analyte comprising the biomarker to dissociate the second helix strand from the first helix strand and displace the reporter particle relative to the analysis substrate;

producing, by the analysis substrate, a biomarker electrical signal in response to the chemical analyte contacting the DNA switch;

receiving, by the transduction member, the biomarker electrical signal from the analysis substrate and producing a transduction signal from the biomarker electrical signal;

determining the impedance of the analysis substrate from the transduction signal;

estimating kinetic rate constants for each contact between the chemical analyte and the DNA switch; and combining the kinetic rate constants and producing a mean kinetic rate constant with uncertainty quantification for the kinetic rate constants;

aggregating the mean kinetic rate constants for the plurality of agile nucleic acid sensor in the agile nucleic acid sensor array; and producing a kinetic fingerprint for the chemical analyte from the mean kinetic rate constants.

2. The process of claim 1, further comprising:

reading the kinetic fingerprint from the agile nucleic acid sensor array;

providing the kinetic fingerprint as input to a machine learning model for classification;

providing the kinetic fingerprint as input to an AI-enhanced simulator;

updating training data for the AI-enhanced simulator machine learning models;

providing a physical model of the agile nucleic acid sensor and kinetic fingerprint measurement to the AI-enhanced simulator machine learning models;

combining the kinetic fingerprint, physical models, and parameter uncertainties using machine learning model to generate physics enhanced training data with uncertainty quantification; and combining AI-enhanced simulator training data with the sensor array kinetic fingerprint by analyte classification machine learning to produce analyte classification with uncertainty quantification.

* * * * *